US 6,712,772 B2

(12) United States Patent
Cohen et al.

(10) Patent No.: US 6,712,772 B2
(45) Date of Patent: Mar. 30, 2004

(54) LOW POWER CONSUMPTION IMPLANTABLE PRESSURE SENSOR

(75) Inventors: Ehud Cohen, Ganei Tikva (IL); Shai Vaingast, Yehud (IL)

(73) Assignee: Biocontrol Medical Ltd., Yehud (IL)

( * ) Notice: Subject to any disclaimer, the term of this patent is extended or adjusted under 35 U.S.C. 154(b) by 55 days.

(21) Appl. No.: 10/076,869

(22) Filed: Feb. 15, 2002

(65) Prior Publication Data

US 2003/0100839 A1 May 29, 2003

Related U.S. Application Data

(63) Continuation-in-part of application No. 09/996,668, filed on Nov. 29, 2001.

(51) Int. Cl.$^7$ .............................. A61B 5/02; A61B 5/00; G01L 27/00
(52) U.S. Cl. ...................... 600/561; 600/485; 600/486; 73/1.57
(58) Field of Search ................................. 600/486, 481, 600/485, 488, 300, 377, 373, 561; 73/1.57

(56) References Cited

U.S. PATENT DOCUMENTS

| 3,628,538 A | 12/1971 | Vincent et al. |
|---|---|---|
| 3,640,284 A | 2/1972 | De Langis |
| 3,866,613 A | 2/1975 | Kenny et al. |
| 3,870,051 A | 3/1975 | Brindley |
| 3,926,178 A | 12/1975 | Feldzamen |
| 3,941,136 A | 3/1976 | Bucalo |
| 3,983,865 A | 10/1976 | Shepard |
| 3,983,881 A | 10/1976 | Wickham |
| 4,023,562 A | 5/1977 | Hynecek et al. |
| 4,023,574 A | 5/1977 | Nemec |
| 4,106,511 A | 8/1978 | Erlandsson |
| 4,136,684 A | 1/1979 | Scattergood et al. |

(List continued on next page.)

FOREIGN PATENT DOCUMENTS

| WO | WO 00/19939 | 4/2000 |
|---|---|---|
| WO | WO 00/19940 | 4/2000 |

OTHER PUBLICATIONS

Fall, et al., "Electrical Stimulation in Interstitial Cystitis", Journal of Urology, 123(2), pp. 192–195, Feb. 1980.

Zermann, et al., "Sacral Nerve Stimulation for Pain Relief in Interstitial Cystitis", Urol. Int., 65(2), pp. 120–121, 2000.

Chai, et al., "Percutaneous Sacral Third Nerve Root Neurostimulation Improves Symptoms and Normalizes Urinary HB–EGF Levels and Antiproliferative Activity in Patients with Interstitial Cystitis", Urology, 55(5), pp. 643–646, May 2000.

(List continued on next page.)

*Primary Examiner*—Max F. Hindenburg
*Assistant Examiner*—Navin Natnithithadha
(74) *Attorney, Agent, or Firm*—Ladas & Parry

(57) ABSTRACT

Pressure-measuring apparatus is provided, including a battery and a pressure transducer. The pressure transducer is adapted to be placed in a patient, and has a characteristic mechanical response bandwidth f, and a corresponding mechanical response period p equal to 1/f. A control unit is adapted to actuate the battery to drive current through the pressure transducer for a current-driving time period less than 0.5 p, and to sense an electrical characteristic of the pressure transducer during the current-driving time period.

276 Claims, 6 Drawing Sheets

U.S. PATENT DOCUMENTS

| | | |
|---|---|---|
| 4,139,006 A | 2/1979 | Corey |
| 4,153,059 A | 5/1979 | Fravel et al. |
| 4,157,087 A | 6/1979 | Miller et al. |
| 4,165,750 A | 8/1979 | Aleev et al. |
| 4,177,819 A | 12/1979 | Kofsky et al. |
| 4,222,377 A | 9/1980 | Burton |
| 4,290,420 A | 9/1981 | Manetta |
| 4,406,288 A | 9/1983 | Horwinski et al. |
| 4,407,296 A | 10/1983 | Anderson |
| 4,432,372 A | 2/1984 | Monroe |
| 4,457,299 A | 7/1984 | Cornwell |
| 4,492,233 A | 1/1985 | Petrofsky et al. |
| 4,515,167 A | 5/1985 | Hochman |
| 4,542,753 A | 9/1985 | Brenman et al. |
| 4,568,339 A | 2/1986 | Steer |
| 4,571,749 A | 2/1986 | Fischell |
| 4,580,578 A | 4/1986 | Barson |
| 4,607,639 A | 8/1986 | Tanagho et al. |
| 4,688,575 A | 8/1987 | DuVall |
| 4,731,083 A | 3/1988 | Fischell |
| 4,739,764 A | 4/1988 | Lue et al. |
| 4,785,828 A | 11/1988 | Maurer |
| 4,825,876 A | 5/1989 | Beard |
| 4,846,191 A | 7/1989 | Brockway et al. |
| 4,873,986 A | 10/1989 | Wallace |
| 4,881,526 A | 11/1989 | Johnson et al. |
| 5,113,868 A * | 5/1992 | Wise et al. .................. 600/488 |
| 5,184,619 A | 2/1993 | Austin |
| 5,207,103 A * | 5/1993 | Wise et al. .................... 73/724 |
| 5,285,781 A | 2/1994 | Brodard |
| 5,291,902 A | 3/1994 | Carman |
| 5,330,505 A | 7/1994 | Cohen |
| 5,423,329 A | 6/1995 | Ergas |
| 5,452,719 A | 9/1995 | Eisman et al. |
| 5,484,445 A | 1/1996 | Knuth |
| 5,522,266 A | 6/1996 | Nicholson et al. |
| 5,562,717 A | 10/1996 | Tippey et al. |
| 5,564,434 A | 10/1996 | Halperin et al. |
| 5,566,680 A | 10/1996 | Urion et al. |
| 5,807,397 A | 9/1998 | Barreras |
| 5,927,282 A | 7/1999 | Lenker et al. |
| 5,969,591 A | 10/1999 | Fung |
| 6,002,964 A | 12/1999 | Feler et al. |
| 6,131,575 A | 10/2000 | Lenker et al. |
| 6,135,945 A | 10/2000 | Sultan |
| 6,221,024 B1 | 4/2001 | Miesel |
| 6,238,423 B1 | 5/2001 | Bardy |
| 6,240,315 B1 | 5/2001 | Mo et al. |
| 6,240,316 B1 | 5/2001 | Richmond et al. |
| 6,248,083 B1 | 6/2001 | Smith et al. |
| 6,572,543 B1 * | 6/2003 | Christopherson et al. ... 600/300 |
| 6,585,660 B2 * | 7/2003 | Dorando et al. ............ 600/486 |

OTHER PUBLICATIONS

P. D. O'Donnell ed., *Urinary Incontinence*, Chap. 26, 1997, Mosby Publishers, St. Louis, MI pp. 197–202.

Caraballo, et al., "Sacral Nerve Stimulation as a Treatment for urge Incontinence and Associated Pelvic Floor Disorders at a Pelvic Floor Center: A Follow–Up Study", Urology, 57(6 Suppl 1), p. 121, Jun. 2001.

U.S. patent application No.: 09/413,272, entitled: "Incotinence Treatment Device", filed Oct. 6, 1999.

Medtronic®'s InterStim Therapy for Urinary Control–Patient Stories, 1997, Nedtronic Inc., Spring Lake Park, MN, 2 pages. (http://webprod1.medtronic.com/neuro/interstim/4Bsize.html).

Summary of Safety and Effectiveness of Medtronic® Interstim® Sacral Nerve Stimulation (SNS)TM System, Sep. 1997, Medtronic Inc., Spring Lake Park, MN, 2 pages.

Medtronic®'s InterStim Therapy for Urinary..: for People with Bladder Control Problem, 1997, Medtronic Inc., Spring Lake Park, MN, 2 pages. (http://webprod1.medtronic.com/neuro/interstim/1types.html).

* cited by examiner

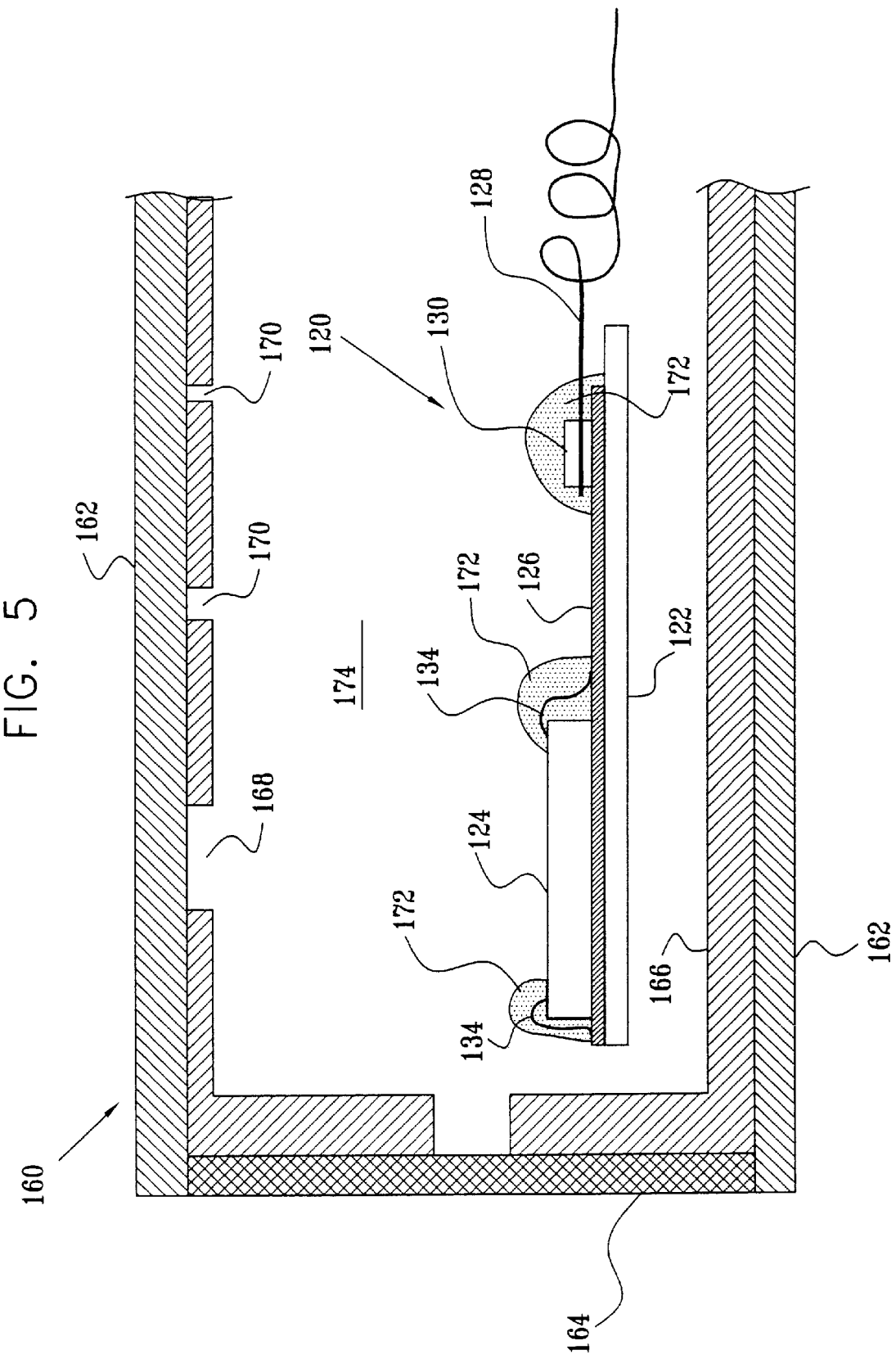

LOW POWER CONSUMPTION IMPLANTABLE PRESSURE SENSOR

CROSS-REFERENCES TO RELATED APPLICATIONS

This application is a continuation-in-part of a U.S. patent application Ser. No. 09/996,668, entitled, "Pelvic disorder treatment device," filed Nov. 29, 2001, which shares common inventorship with the inventorship of the present patent application, is assigned to the assignee of the present patent application, and is incorporated herein by reference.

FIELD OF THE INVENTION

The present invention relates generally to implantable medical devices, and specifically to implantable pressure sensors.

BACKGROUND OF THE INVENTION

A significant effort has been underway for many years to develop implantable medical devices for direct measurement of physiological parameters of a patient for both temporary and chronic use. Some prior art devices cannot be implanted in the body due to their undesirably large size, limited life span, or high power consumption Challenges exist, for example, in developing efficient commercial pressure transducers, capable of being used in the body of a patient for direct measurement of physiologic pressures such as urinary bladder, abdominal, respiratory, cardiac, venous, arterial, amniotic, and cerebrospinal fluid pressures. For example, suitable implantable cardiac pressure sensors which have very low power consumption for tracking the condition of a heart failure patient are not available.

U.S. Pat. No. 6,248,083 to Smith et al., U.S. Pat. No. 5,969,591 to Fung, U.S. Pat. No. 5,566,680 to Urion et al., U.S. Pat. No. 5,522,266 to Nicholson et al., U.S. Pat. No. 5,184,619 to Austin, U.S. Pat. No. 4,873,986 to Wallace, and U.S. Pat. No. 4,825,876 to Beard, which are incorporated herein by reference, describe the use of piezoresistive elements to facilitate pressure measurements for medical applications.

U.S. Pat. No. 4,407,296 to Anderson, which is incorporated herein by reference, describes a hermetically-sealed piezoresistive pressure transducer for implantation in the body.

U.S. Pat. No. 4,846,191 to Brockeway et al., which is incorporated herein by reference, describes an implantable device for chronic measurement of internal body pressures. The device may include a piezoresistive element.

U.S. Pat. No. 4,023,562 to Hynecek et al., which is incorporated herein by reference, describes an implantable piezoresistive pressure transducer for monitoring internal fluid or pneumatic pressures within the body.

U.S. Pat. No. 4,432,372 to Monroe, which is assigned to Medtronic, Inc. and is incorporated herein by reference, describes apparatus for multiplexing the power and signal leads of an implantable piezoelectric pressure transducer. A device built according to the description in the Monroe patent charges a capacitor located at the pressure transducer site, and, subsequently, allows the capacitor to discharge through a Wheatstone bridge. The capacitor is a fundamental component of this device, as it permits the time-sharing of power functions and sensing functions into only two wires. Although not stated in the Monroe patent, it is known that repeated charging and discharging of capacitors is often associated with significant heat dissipation, and, therefore, increased energy consumption.

U.S. Pat. No. 6,221,024 to Miesel, which is also assigned to Medtronic, Inc. and is incorporated herein by reference, describes a method for sealing oil-filled pressure transducer modules for a chronically-implantable pressure sensor lead. The '024 patent states: "U.S. Pat. No. 4,023,562 describes a pressure transducer comprising a piezoresistive bridge of four, orthogonally disposed, semiconductor strain gauges formed interiorly on a single crystal silicon diaphragm area of a silicon base. A protective silicon cover is bonded to the base around the periphery of the diaphragm area to form a sealed, evacuated chamber. Deflection of the diaphragm due to ambient pressure changes is detected by the changes in resistance of the strain gauges. Because the change in resistance is so small, a high current is required to detect the voltage change due to the resistance change. The high current requirements render the piezoresistive bridge unsuitable for long term use with an implanted power source. High gain amplifiers that are subject to drift over time are also required to amplify the resistance-related voltage change."

U.S. Pat. No. 5,564,434 to Halperin et al., which is incorporated herein by reference, describes an endocardial lead for implantation in a heart chamber. The lead is able to sense pressure changes via capacitors, and transmit information responsive to the pressure changes to an internal or external medical device.

U.S. Pat. No. 5,330,505 to Cohen, which is incorporated herein by reference, describes implantable sensors for sensing a variety of cardiac physiologic signals.

U.S. Pat. No. 6,238,423 to Bardy, which is incorporated herein by reference; describes apparatus for treating chronic constipation, which includes an implantable pressure sensor for sensing tension in a wall of the digestive system.

U.S. Pat. No. 6,240,316 to Richmond et al., which is incorporated herein by reference, describes the use of implanted pressure sensors in apparatus for treating sleep apnea.

Measurement of pressure in the vicinity of the bladder and lower abdominal region is an important element in devices and methods for treating and controlling urinary incontinence. U.S. Pat. No. 6,135,945 to Sultan, which is incorporated herein by reference, describes apparatus for preventing urinary incontinence. The described apparatus includes an implanted pressure sensor for sensing intra-abdominal pressure. U.S. Pat. No. 4,571,749 to Fischell, which is incorporated herein by reference, describes an artificial sphincter device whose pressure can vary in response to changes in abdominal or intravesical (bladder) pressure. U.S. Pat. No. 5,562,717 to Tippey et al., which is incorporated herein by reference, describes electrical stimulation treatment for incontinence and other neuromuscular disorders, and includes a pressure sensor for determining changes in pressure in the vaginal or anal muscles.

PCT Patent Publication WO 00/19939 to Gross et al., entitled "Control of urge incontinence," which is assigned to the assignee of the present patent application and incorporated herein by reference, describes a device for treatment of urinary urge incontinence comprising a system in which imminent involuntary urine flow is sensed, and appropriate nerves or muscles are stimulated to inhibit the flow.

U.S. Patent Publication WO 00/19940 to Gross et al., entitled, "Incontinence treatment device," which is assigned to the assignee of the present patent application and incorporated herein by reference, describes a device for treating urinary stress incontinence comprising a system in which imminent involuntary urine flow is sensed, and nerves or muscles are stimulated to inhibit the flow.

In general, for implanted pressure sensors, issues of size, durability, accuracy and, particularly, power consumption are major considerations that must be addressed in order to ensure that the goals of the application are achieved.

SUMMARY OF THE INVENTION

It is an object of some aspects of the present invention to provide improved apparatus and methods for reducing power consumption in a pressure sensor implanted in the body of a patient.

It is also an object of some aspects of the present invention to provide improved methods and apparatus for reducing heat dissipation in a pressure sensor implanted in the body of a patient.

It is a further object of some aspects of the present invention to provide improved apparatus and methods for increasing the useful lifetime of an implantable device.

It is yet a further object of some aspects of the present invention to provide improved methods for enabling the coupling of MP35N wires and other materials in lead wires to circuitry in an implantable device.

It is still a further object of some aspects of the present invention to provide less-complicated methods and apparatus for producing an implantable device.

It is also an object of some aspects of the present invention to provide improved methods and apparatus for producing a low cost implantable device.

In preferred embodiments of the present invention, apparatus to achieve the above objects comprises at least one implantable pressure-sensing device coupled to a control unit. The sensing device is preferably implanted in a patient's body at a location chosen in accordance with the particular condition being treated or diagnostic procedure being performed. Preferably, the sensing device comprises an element characterized by electrical resistance that varies as a function of the pressure imposed upon it, typically a piezoresistive element. The pressure measuring apparatus is preferably designed such that the piezoresistive element of the sensing device is integrated into a Wheatstone bridge electrical circuit as one of the four resistors (typically adapting techniques described in one or more of the references cited hereinabove and incorporated herein by reference). Alternatively, two or more of the resistors in the Wheatstone bridge include piezoresistive elements. The sensing device operates by receiving a designated driving signal from the control unit and, as a function of the pressure upon it, undergoing a change in resistance that causes a measurable variation in the voltage output of the Wheatstone bridge. The driving signal includes a series of relatively short duration, low duty cycle pulses.

Consequently, in preferred embodiments of the present invention, the actual time during which the apparatus consumes power by driving current through the Wheatstone bridge and taking measurements is significantly less than the total time of operation of the apparatus. In prior art implantable piezoresistive pressure sensors, by contrast, a major shortcoming is high power consumption, which limits usable lifetime and imposes demanding requirements upon power supplies, such as batteries.

Electrical leads for implantable medical devices are often composed of MP35N or platinum/iridium (Pt/Ir), or, less commonly, alloys having iron in low quantities (e.g., moderately or significantly less than 60% iron by weight), as these materials have proven to be both safe and effective for many applications in the human body. A problem with using MP35N (or these other materials) for electrical leads is that it does not solder well to copper, which is a common conductor in electrical circuits. In particular, increasing iron content is associated with increased facility in soldering, but decreased biocompatibility. MP35N and Pt/Ir, having essentially no iron, are particularly difficult to solder using standard techniques. The following solution, and that elaborated more completely in the Detailed Description of Preferred Embodiments, while described with respect to MP35N by way of illustration, applies as well to platinum/iridium and other alloys having low iron content (e.g., 1–60% iron, 1–40% iron, or 1–20% iron). Additionally, it applies to DFT wire (Fort Wayne Metals, Fort Wayne, Ind.) and other similar types of lead wires, in which a highly-conductive core is surrounded by a less conductive, more biocompatible outer surface. For example, the techniques described herein may be applied to a lead wire having MP35N over a silver core.

In preferred embodiments of the present invention, MP35N wires are used to connect the control unit to a circuit in an implanted pressure sensor or other medical device. The problem of securely connecting the MP35N wire to the circuit board is overcome by using an intermediate conductor to couple MP35N wires to the circuit. In some preferred embodiments, a stainless steel cylinder is mechanically coupled to an MP35N wire, for example by crimping. The stainless steel cylinder is then soldered to the circuit board. In other preferred embodiments, the cylinder comprises other biocompatible conductors, suitable for being mechanically coupled to the MP35N wire and for soldering to the circuit board. In further preferred embodiments of the present invention, the solder used to couple the MP35N wire and the circuit board comprises indium, preferably a high percentage of indium, as the inventors have found that this facilitates good electrical coupling of the MP35N wire and the circuit board, even without the use of stainless steel cylinders.

In order for the electrical circuit comprising the pressure measuring apparatus to function properly inside the human body, it must be protected from the generally electronics-incompatible environment at the implant location. Additionally, the device must be robust enough to survive the implant procedure. Thus, in preferred embodiments of the present invention, the electrical circuit in the pressure measuring apparatus and the connections to the MP35N wires are secured inside a hollow stainless steel tube or other casing comprising a sensing hole through which pressure changes can be measured. Preferably, the tube is filed with a generally-incompressible biocompatible substance that efficiently conveys pressure changes, such as a silicon gel. The tube has one or more gel-transport holes through which the gel can be added, while excess gel is forced through the sensing hole and/or the other gel-transport holes, such that all air bubbles are forced out of the tube. Optionally, the gel-transport holes may include the sensing hole. It is important to remove any air bubbles in order to obtain accurate pressure measurements, as air bubbles in the gel reduce the sensitivity of the pressure sensor.

Preferably, the sensor is coated with a protective substance, such as parylene, to protect it from external moisture. In a preferred embodiment, the stainless steel tube is further encased in a flexible tube, such as one made of silicone, which is able to convey pressure fluctuations through the sensing hole to the pressure sensor, while maintaining the integrity of the sensor and the gel.

There is therefore provided, in accordance with a preferred embodiment of the present invention, pressure-measuring apparatus, including:

a battery;

a pressure transducer, which is adapted to be placed in a patient, the pressure transducer having a characteristic mechanical response bandwidth f, and a corresponding mechanical response period p equal to 1/f; and a control unit, which is adapted to actuate the battery to drive current through the pressure transducer for a current-driving time period less than 0.5 p, and to sense an electrical characteristic of the pressure transducer during the current-driving time period.

Typically, the pressure transducer is adapted to be implanted in the patient. Alternatively, the pressure transducer is adapted to be incorporated in a catheter.

For some applications, the pressure transducer is adapted to measure an abdominal pressure of the patient, a pressure of a urinary bladder of the patient, a cardiac pressure of the patient, or a blood pressure of the patient.

The pressure transducer preferably includes a piezoresistive pressure transducer, incorporated in a Wheatstone bridge circuit.

In a preferred embodiment, the control unit is adapted to set the current-driving time period to be less than 1000 microseconds. The control unit is typically adapted to designate an initial portion of the current-driving time period as a pressure-transducer stabilization period, during which the control unit withholds from sensing the characteristic.

As appropriate, the control unit may be adapted such that, in sensing the electrical characteristic, the control unit senses a current passing through the pressure transducer and/or a voltage drop across two points of the pressure transducer. The control unit is preferably adapted to sense the electrical characteristic substantially only during the current-driving time period.

Preferably, the control unit is adapted to actuate the battery to expend less than 5 microjoules in driving the current through the pressure transducer. Moreover, the control unit is preferably adapted to actuate the battery to drive the current directly into the pressure transducer, substantially without charging a capacitor located at a placement site of the pressure transducer. In particular, the control unit is preferably adapted to actuate the battery to drive the current directly into the pressure transducer, substantially without charging a capacitor located at a placement site of the pressure transducer having capacitance greater than 0.1 nF.

Additionally, in a preferred embodiment, the control unit is adapted to actuate the battery to drive current into the pressure transducer during a plurality of current-driving time periods, each less than 0.5 p, and to sense respective electrical characteristics of the pressure transducer during each of the current-driving time periods. In this case, the battery is preferably adapted to drive the current directly into the pressure transducer, substantially without charging a capacitor located at a placement site of the pressure transducer during each of the current-driving time periods.

For some applications, the control unit is adapted to actuate the battery to drive current through the pressure transducer during a plurality of current-driving time periods, each less than 0.5 p. Additionally, a duty cycle of the control unit (defined by a length of one of the current-driving time periods divided by a time between the initiation of two successive current-driving time periods) is preferably less than 0.3%, or even less than 0.03%.

In a preferred embodiment, the apparatus includes a signal processor, adapted to be placed in the patient at a common placement site with the pressure transducer and to process the sensed electrical characteristic. For example, the signal processor may include an amplifier, adapted to amplify the sensed electrical characteristic. Alternatively or additionally, the signal processor includes a microprocessor. In this case, the apparatus preferably includes:

a first set of wires, adapted to couple the control unit to the microprocessor; and a second set of wires, adapted to couple the microprocessor to the pressure transducer, wherein the number of wires in the second set of wires is greater than the number of wires in the first set of wires.

As appropriate, the control unit may be adapted to set the current-driving time period to be less than 0.1 p, less than 0.02 p, or even less than 0.004 p.

In some preferred embodiments of the present invention, the control unit is adapted: (a) to actuate the battery to drive current through the pressure transducer during a plurality of current-driving time periods, each less than 0.5 p, (b) to sense respective electrical characteristics of the pressure transducer during each of the current-driving time periods, and (c) to space the current-driving time periods by at least ten milliseconds. For some applications, the control unit is adapted to space the current-driving time periods by at least one second, by at least one minute, or even by at least one hour.

There is further provided, in accordance with a preferred embodiment of the present invention, pressure-measuring apparatus, including:

a pressure transducer, which is adapted to be placed at a pressure-sensing site in a patient, the pressure transducer having a characteristic mechanical response bandwidth f, and a corresponding mechanical response period p equal to 1/f; and a control unit, adapted to be placed at a control-unit site at least 3 cm from the pressure-sensing site, to drive current through the pressure transducer for a current-driving time period less than 0.5 p, and to sense an electrical characteristic of the pressure transducer during the current-driving time period.

In a preferred embodiment, the control unit is adapted to be placed at a control-unit site which is at least 5 cm from the pressure-sensing site.

There is still further provided, in accordance with a preferred embodiment of the present invention, pressure-measuring apparatus, including:

a battery;

a pressure transducer, which is adapted to be placed in a patient; and a control unit, which is adapted to actuate the battery to drive current through the pressure transducer for a current-driving time period less than 1000 microseconds, and to sense an electrical characteristic of the pressure transducer during the current-driving time period.

For some applications, the control unit is adapted to set the current-driving time period to be less than 250 microseconds, less than 50 microseconds, less than 10 microseconds, or even less than 2 microseconds.

There is yet further provided, in accordance with a preferred embodiment of the present invention, pressure-measuring apparatus, including:

a pressure transducer, which is adapted to be placed at a pressure-sensing site in a patient; and a control unit, adapted to be placed at a control-unit site at least 3 cm from the pressure-sensing site, to drive current through the pressure transducer for a current-driving time period less than 1000 microseconds, and to sense an electrical characteristic of the pressure transducer during the current-driving time period.

There is also provided, in accordance with a preferred embodiment of the present invention, a method for measuring pressure via a pressure transducer, placed in a patient, the pressure transducer having a characteristic mechanical response bandwidth f, and a corresponding mechanical response period p equal to 1/f, the pressure transducer being coupled to a battery, the method including:
actuating the battery to drive current through the pressure transducer for a current-driving time period less than 0.5 p; and
sensing an electrical characteristic of the pressure transducer during the current-driving time period.

There is additionally provided, in accordance with a preferred embodiment of the present invention, a method for measuring pressure via a pressure transducer, placed in a patient at a pressure-sensing site, the pressure transducer having a characteristic mechanical response bandwidth f, and a corresponding mechanical response period p equal to 1/f, the method including:
from a control-unit site at least 3 cm from the pressure-sensing site, driving current through the pressure transducer for a current-driving time period less than 0.5 p; and
sensing an electrical characteristic of the pressure transducer during the current-driving time period.

There is still additionally provided, in accordance with a preferred embodiment of the present invention, a method for measuring pressure via a pressure transducer, placed in a patient, the pressure transducer being coupled to a battery, the method including:
actuating the battery to drive current through the pressure transducer for a current-driving time period less than 1000 microseconds; and
sensing an electrical characteristic of the pressure transducer during the current-driving time period.

There is yet additionally provided, in accordance with a preferred embodiment of the present invention, apparatus which is adapted to be placed in a patient, including:
circuitry, which is adapted to be placed in a patient;
a lead wire; and
an electrically-conductive connector, which is crimped to the lead wire so as to be electrically coupled thereto, and which is soldered to the circuitry.

Typically, the lead wire includes an MP35N lead wire, a platinum/iridium lead wire, or a wire including 1–60% iron by weight.

In a preferred embodiment, the connector includes a hollow tube, wherein a portion of the lead wire is disposed within the hollow tube, and wherein the hollow tube is crimped to the portion of the lead wire. Typically, but not necessarily, the connector includes stainless steel.

For some applications, the circuitry is adapted to be implanted in the patient. For other applications, the circuitry is adapted to be incorporated in a catheter.

In a preferred embodiment, the circuitry includes a sensor, such as a pressure sensor, a temperature sensor, and/or a chemical sensor. Alternatively or additionally, the sensor includes an electrode, adapted to sense electrical activity in tissue of the patient where the apparatus is placed. Further alternatively or additionally, the sensor includes a flow sensor, adapted to sense a flow of blood in a vicinity of the apparatus.

For some applications, the circuitry includes an active element, such as a stimulating electrode, a light source adapted to facilitate photodynamic therapy, an electroactive polymer, and/or a mechanical actuator.

There is also provided, in accordance with a preferred embodiment of the present invention, apparatus which is adapted to be placed in a patient, including:
circuitry, which is adapted to be placed in the patient;
a lead wire, selected from the group consisting of: an MP35N lead wire, a platinum/iridium lead wire, and lead wire including 1–60% iron by weight; and
solder, including at least 20% indium by weight, for electrically coupling the lead wire to the circuitry.

In a preferred embodiment, the solder includes at least 50% indium.

There is further provided, in accordance with a preferred embodiment of the present invention, apparatus which is adapted to be placed in a patient, including:
an electronic device;
a gel; and
a hollow casing, one or more holes being disposed in a wall thereof, inside which casing the electronic device and the gel are disposed, the casing being configured to facilitate flow of some of the gel out of the one or more holes when the casing is being filled with the gel.

Preferably, the apparatus includes including a flexible covering, adapted to fit around at least a portion of the hollow casing. In a preferred embodiment, the flexible covering includes a flexible silicon covering.

Typically, the hollow casing includes a rigid hollow casing, e.g., a hollow stainless steel casing.

For some applications, the circuitry includes a pressure sensor, disposed within the casing such that pressure changes at a patient site where the apparatus is placed are conveyed to the pressure transducer via the gel.

In a preferred embodiment, a sensing hole is disposed in the hollow casing, and a substantially non-metallic flexible covering is disposed outside the casing, so as to cover the sensing hole and to convey pressure changes at the patient site through the sensing hole to the gel. The diameter of the sensing hole is typically less than 2 mm.

The present invention will be more fully understood from the following detailed description of the preferred embodiments thereof, taken together with the drawings, in which:

BRIEF DESCRIPTION OF THE DRAWINGS

FIG. 5 is a sectional schematic diagram of an implantable pressure transducer, in accordance with a preferred embodiment of the present invention.

DETAILED DESCRIPTION OF PREFERRED EMBODIMENTS

Figure 1:
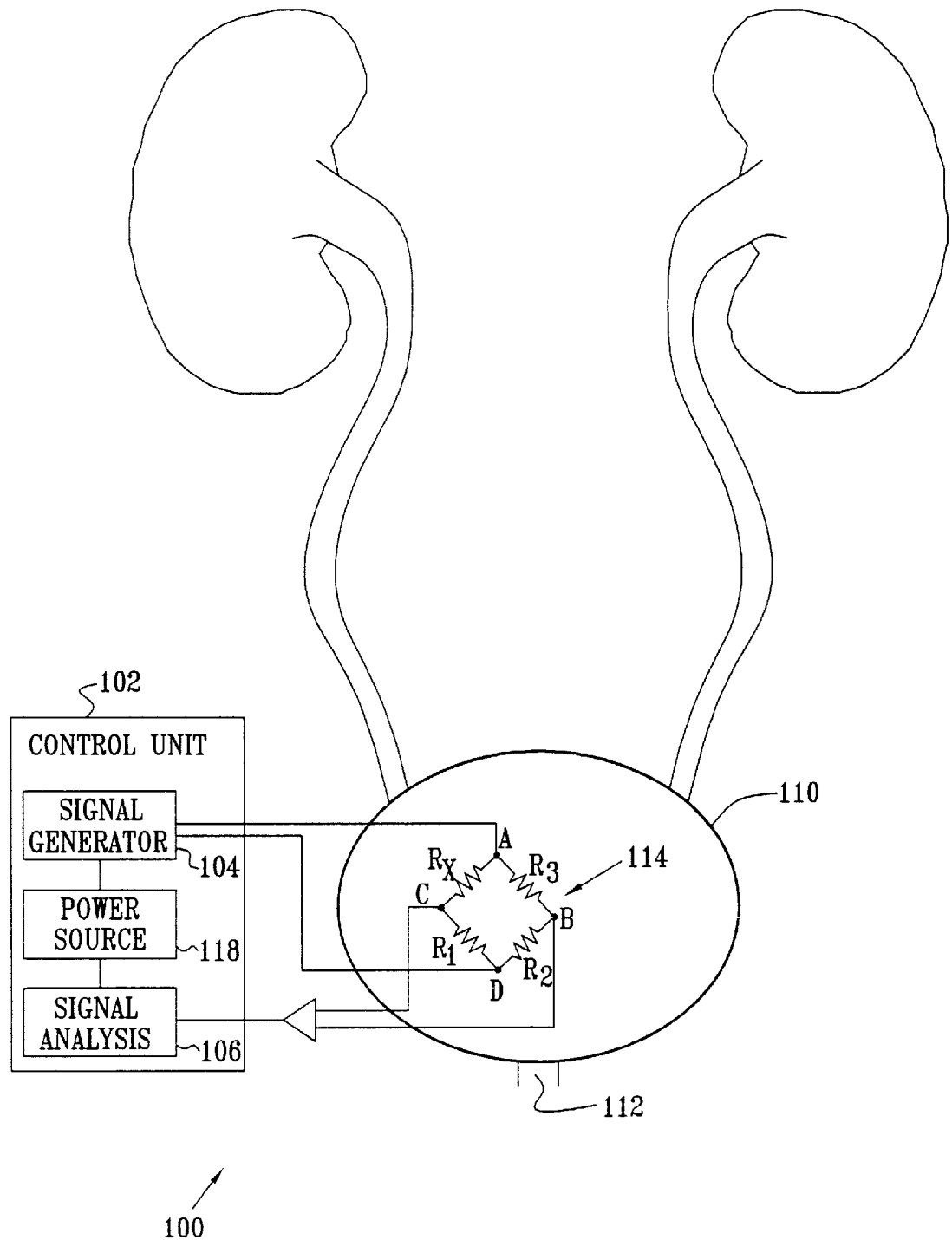
FIG. 1 is a schematic diagram of an implanted pressure measuring system, in accordance with a preferred embodiment of the present invention.

FIG. 1 is a schematic diagram of an implanted pressure measurement system 100, in accordance with a preferred embodiment of the present invention. The example shown is a system for measuring pressure in the urinary bladder 110 of a patient, although it is to be appreciated that system 100 could be implanted to measure pressure at any of a number of appropriate sites in the patient's body, e.g., at a cardiac site.

System 100 typically includes an implantable or external control unit 102 including a signal generator 104, a signal analysis unit 106, and an implantable pressure sensor 114. Typically, pressure sensor 114 includes a piezoresistive element $R_x$ which is electrically connected as one element in a Wheatstone bridge circuit arrangement. For some applications, two or more piezoresistive elements are incorporated into corresponding respective positions in a Wheatstone bridge. A power source 118 is preferably included within control unit 102, and is coupled to provide energy to signal generator 104 and signal analysis unit 106 from rechargeable or non-rechargeable batteries or another replaceable or renewable source of power.

Signal generator 104 sends pulsed signals to pressure sensor 114. Pressure sensor 114, which includes piezoresistive element $R_x$ whose resistance is a function of the pressure imposed upon it, returns a voltage signal (measured between points B and C in the Wheatstone bridge) to control unit 102 commensurate with the value of resistance $R_x$ at the instant of measurement. This voltage signal is amplified and input to signal analysis unit 106 where it is interpreted as a pressure measurement.

Typically, Wheatstone bridges used in prior art implantable medical devices require a relatively large amount of power to operate, as it is the practice to apply cower generally continuously, and to sample intermittently, in order to obtain a signal. Thus, continuous monitoring with a Wheatstone bridge is not efficient in an implanted device, which necessarily has a limited power supply. The positive aspects of a Wheatstone bridge, namely that it is simple, inexpensive, and sensitive to small changes, have therefore not been able to be efficiently utilized using the continuous-operation modes associated therewith in the prior art.

In order to take advantage of the positive aspects of the Wheatstone bridge, while minimizing power consumption, preferred embodiments of the present invention provide for current to be driven through the Wheatstone bridge and for measurements to be taken intermittently, as opposed to continuously. Thus, signals are preferably driven from signal generator 104 to pressure sensor 114 in the form of intermittent pulses.

The delay between successive pressure readings is preferably determined based on the particular application. For example, a single daily blood pressure measurement may be sufficient for some applications, such that the total power requirement is negligible. Cardiac pressure measurements, intended for example to track heart failure, may be performed at 5 Hz. A system for identifying the onset of stress incontinence may sample at 30 Hz. Further, because action potential propagation is associated with mechanical deformations of axons, pressure changes responsive to these deformations may be sampled at 2000 Hz.

In general, these embodiments of the present invention are significantly more efficient than piezoresistive pressure-sampling methods known in the art, because these embodiments commonly perform sampling during intermittent short time periods whose reciprocals correspond to sampling rates 2, 100, or even 1000 times higher than the characteristic mechanical response bandwidth of the piezoresistive pressure sensors For example, in a preferred embodiment of the present invention which samples during intermittent 10 $\mu$sec periods, a sampling pseudo-frequency of 100 kHz is obtained (i.e., the reciprocal of 10 $\mu$sec), far above a 1 kHz bandwidth characteristic of many piezoresistive pressure sensors which are ready for implantation.

It is noted that, in the context of the present patent application and in the claims, the term "characteristic mechanical response bandwidth" refers to the bandwidth in a fully-assembled pressure-sensing device, and not to the theoretical bandwidth attainable, for example, by a piezoresistive circuit unencumbered by gel or supporting structure. Thus, although a given piezoresistive circuit may have a theoretical bandwidth of 10 kHz, once it is incorporated into a fully-assembled pressure-sensing device, the characteristic mechanical response bandwidth of the device would be closer to 1 kHz.

Prior art piezoresistive sampling techniques, by contrast, do not generally drive current through piezoresistive sensors and attempt sampling during time periods whose reciprocals correspond to frequencies substantially faster than the characteristic mechanical response bandwidth of the piezoresistive material. The realization by the inventors that the mechanical frequency response can be decoupled from the electrical bandwidth without adding other heat-dissipating components, so as to enable fast and efficient intermittent sampling, provides a substantial improvement in characteristics of the implanted device over implanted devices known in the art. It is noted that the above-cited U.S. Pat. No. 4,432,372 to Monroe uses fast sampling for a very different purpose (to enable time-sharing of lead wires), and requires the energy-consuming process of charging and discharging of a capacitor to enable every pressure measurement.

Figure 2A:
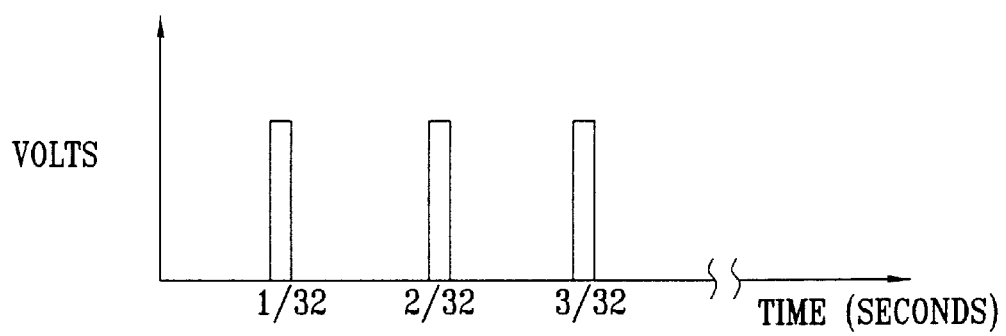
FIGS. 2A and 2B are illustrative examples of power signals driven into a sensing device by a control unit, in accordance with a preferred embodiment of the present invention.
Figure 2B:
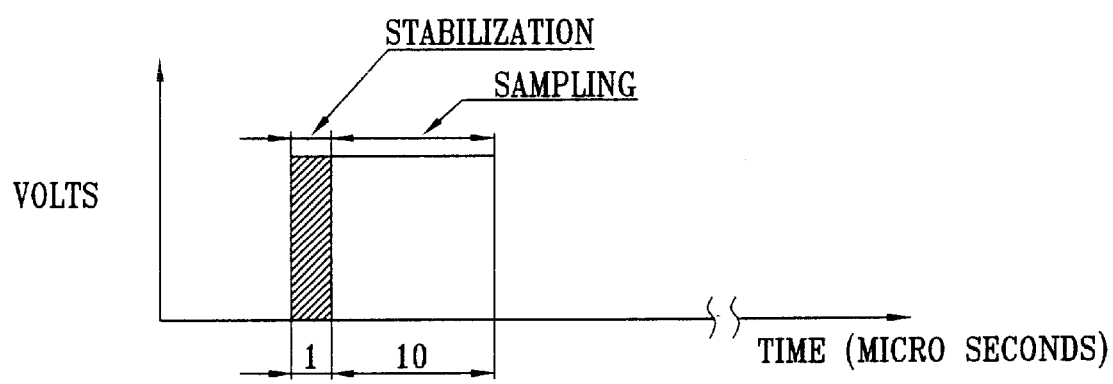

FIGS. 2A and 2B show an illustrative example of a preferred pulse waveform to facilitate measuring pressure in the bladder of a patient, in accordance with a preferred embodiment of the present invention. For some applications, signal generator 104 sends pulses to pressure sensor 114 at a driving rate of 32 Hz (FIG. 2A), although it is to be understood that other driving rates (e.g., between 10 $\mu$Hz and 3 kHz) may also be used, as appropriate for a particular application.

A typical stabilization period for a preferred piezoresistive device upon which pressure is imposed is approximately 1 $\mu$sec. A suitable definition of "stabilization period" for most applications is the time from the first application of current to sensor 114 until the time when the output of the sensor reaches 90% of maximum. In a preferred embodiment, a constant-pressure calibration period of sensor 114 is provided, in which samples are taken at various times after the first application of current to the sensor (e.g., every 100 nanoseconds), until the samples reach a steady-state value. Preferably, a calibration function C(t) is thus determined, to facilitate corrections to be made to data which are sampled during the stabilization period during regular operation of sensor 114. For example, C(t) may represent the percentage of the steady-state pressure reading, such that a corrected pressure reading based on a data point x recorded at t=200 nanoseconds after the first application of current would simply be x/C(t). Advantageously, this method allows the total time during which current is driven through pressure sensor 114 to be very short, e.g., only several tens or hundreds of nanoseconds.

FIG. 2B is a magnified schematic of a typical pulse shown in FIG. 2A with a sampling time of 10 $\mu$sec. For this signal frequency and waveform, the total time that the pressure sensor is activated during one second is the stabilization time plus the sampling time multiplied by the frequency, or 11 μsec×32=352 μsec. Thus, in the embodiment shown in FIG. 2B, no data are typically recorded during the stabilization period. It can be seen that, in comparison to constant pressure sensor activation, as is known in the art, the total power consumption in this example is reduced by a factor of 1/0.000352 or almost 3000. Thus, the issue of power consumption, a major consideration in design of prior art active devices implanted in patients, is significantly reduced in preferred embodiments of the present invention.

In the illustrative examples described above, a low power consumption pressure sensor is described in a preferred embodiment utilizing a piezoresistive element and a Wheatstone bridge arrangement. This is considered as illustrative only of certain aspects of the invention. Since numerous modifications and changes will readily occur to those skilled in the art, it is not desired to limit the invention to the exact construction and operation shown and described. Accordingly, all suitable modifications and equivalents in materials and circuitry that enable a change in resistance or another parameter to be utilized to measure changes in pressure in an implanted device utilizing a low measurement duty cycle may be considered to fall within the scope of the invention. Preferred duty cycles are typically, but not necessarily, below 0.3% or even 0.03%.

Figure 3A:
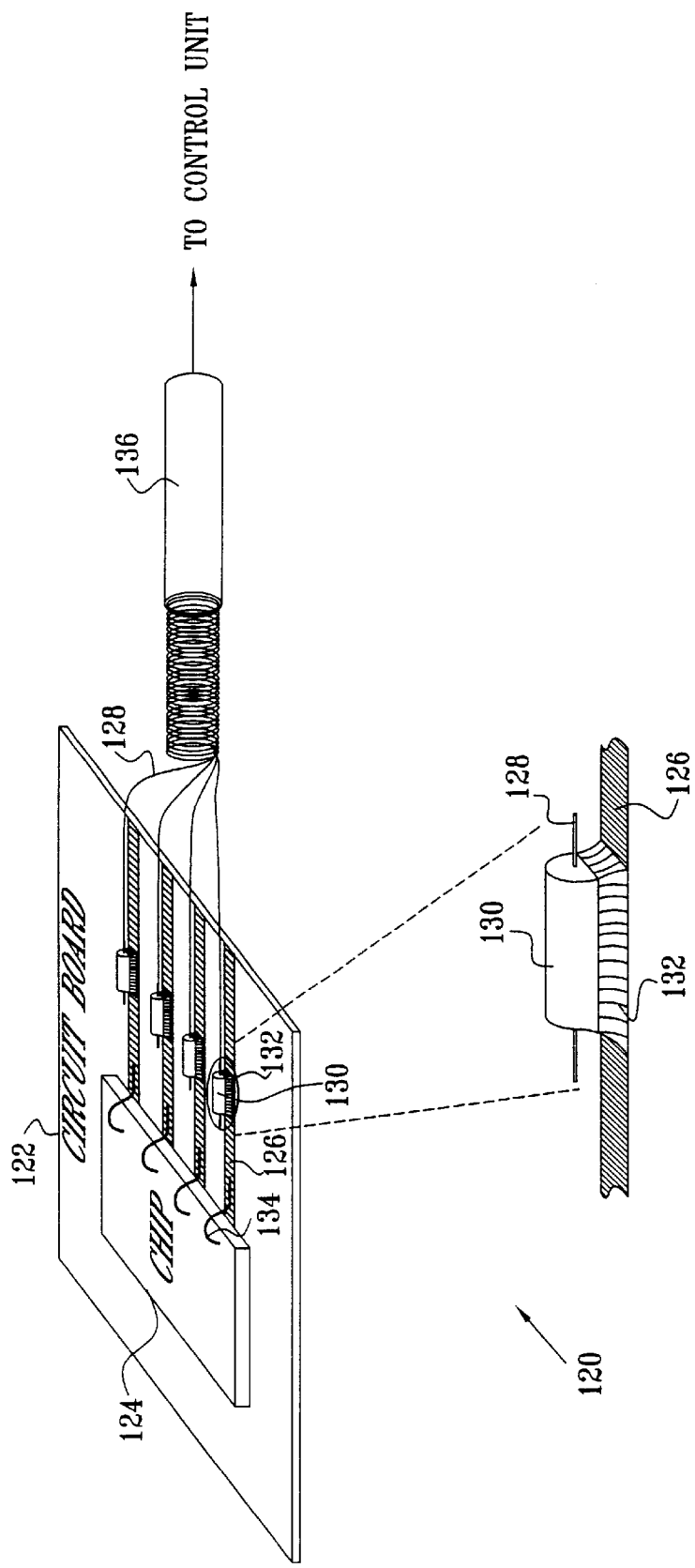
FIGS. 3A and 3B are schematic diagrams of a connection system between MP35N wires and a chip, in accordance with a preferred embodiment of the present invention.
Figure 3B:
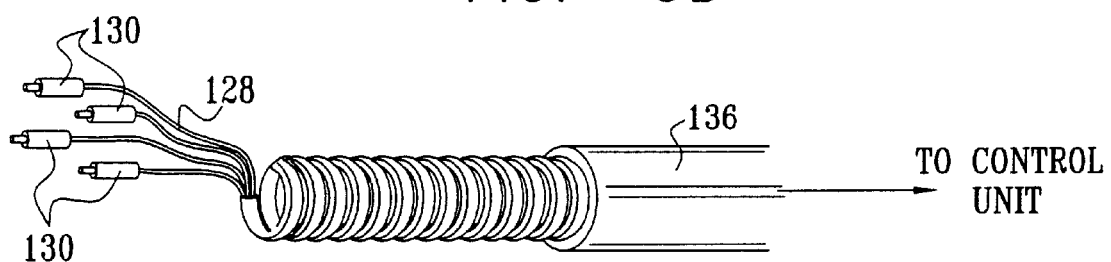

Reference is now made to FIGS. 3A and 3B, which are schematic drawings of a connection system 120 for use, for example, in the implantable pressure sensor described hereinabove with reference to FIG. 1, in accordance with a preferred embodiment of the present invention. It is to be understood, however, that the apparatus and methods described with reference to FIGS. 3A and 3B could alternatively or additionally be applied with a range of circuitry, such as, for example, a signal processor such as a microprocessor, sensors such as pressure sensors other than those described herein, temperature sensors, chemical sensors (e.g., glucose sensors), flow sensors, or sensing electrodes. Further alternatively or additionally, connection system 120 may be used in combination with active elements, such as, by way of illustration and not limitation, actuators, stimulating electrodes, electroactive polymers, or light sources for photodynamic therapy.

In accordance with a preferred embodiment of the present invention, connection system 120 provides means for connecting control unit 102 to pressure sensor 114 (FIG. 1) via MP35N wires 128. MP35N is a preferred alloy for implantable medical devices. Preferably, the pressure sensing means is included in a chip 124, which is fixed to a circuit board 122 including four copper conductive elements 126. Conductive elements 126 are, in turn, coupled to four or more wires 134 which function to transmit signals to and from chip 124.

Coupling MP35N wires 128 to conductive elements 126 is optimally not accomplished by direct soldering, as MP35N wires do not solder satisfactorily to copper. Thus, a stainless steel cylinder 130 is mechanically coupled to the end of each MP35N wire, for example via crimping (FIG. 3B), so as to achieve good electrical contact therewith, and the cylinder is subsequently coupled to conductive elements 126 by a solder joint 132, using techniques known in the art. It is noted that stainless steel can be satisfactorily soldered to copper and is also suitable for chronic implantation in the human body, using known procedures. To obtain improved electrical conduction, cylinders 130 are preferably coated with gold prior to soldering. Alternatively, cylinders 130 are treated with phosphoric acid to improve electrical conduction. Wires 128 are also preferably coated with a substance such as Teflon using standard methods so as to prevent short circuits between the wires. Additionally, the portion of wires 128 between the circuit board and the control unit are preferably wound together into a coil and enclosed in a flexible tube 136 for further protection and ease of handling during implantation.

Figure 4A:
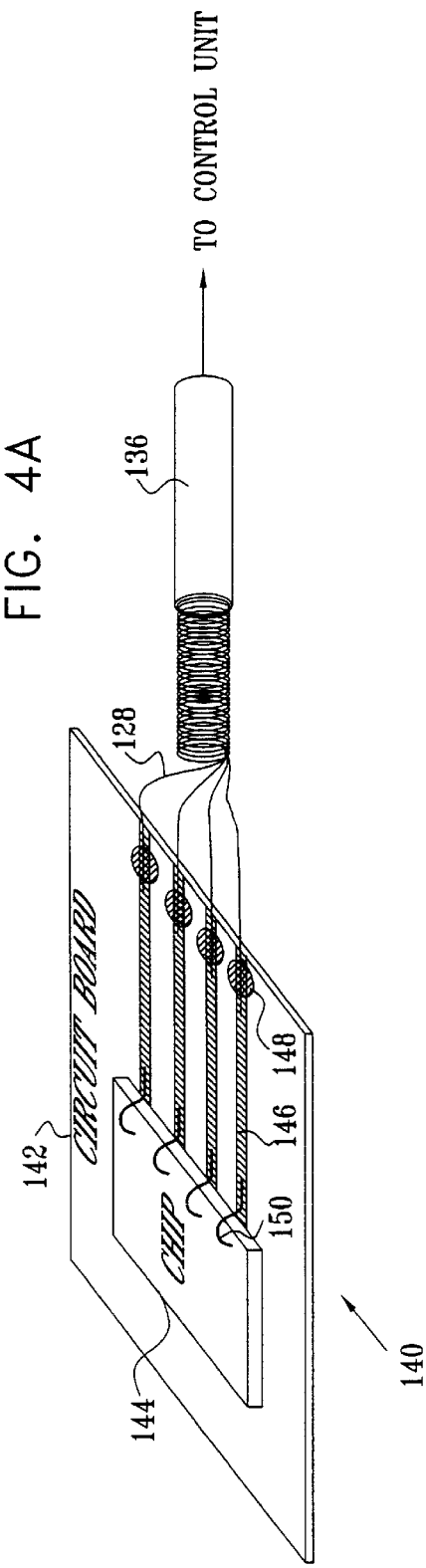
FIGS. 4A and 4B are schematic diagrams of another connection system between MP35N wires and a chip, in accordance with a preferred embodiment of the present invention.

FIG. 4A is a schematic drawing of a connection system 140 for use, for example, in the implantable pressure sensor described hereinabove with reference to FIG. 1, in accordance with a preferred embodiment of the present invention. Alternatively or additionally, it will be appreciated that other medical applications, such as those described hereinabove with reference to FIGS. 3A and 3B, may also be facilitated through the use of connection system 140.

In accordance with a preferred embodiment of the present invention, MP35N wires 128 are used to electrically couple control unit 102 to pressure sensor 114, as described with reference to FIGS. 3A and 3B. This coupling is not optimally achieved by simply soldering MP35N wires to standard copper connectors, as MP35N does not solder satisfactorily to copper using standard tin solder. The inventors have found that MP35N wires do solder satisfactorily when the solder includes a substantial quantity of indium. Therefore, connection system 140, including a chip 144 including pressure sensor 114, is preferably soldered with indium solder joints 148 to conductive elements 146 of a circuit board 142. Chip 144, in turn, is preferably electrically coupled to conductive elements 146 by small connecting wires 150. Preferably, solder joints 148 include at least 10% indium by weight (typically 50–100% indium).

Figure 4B:
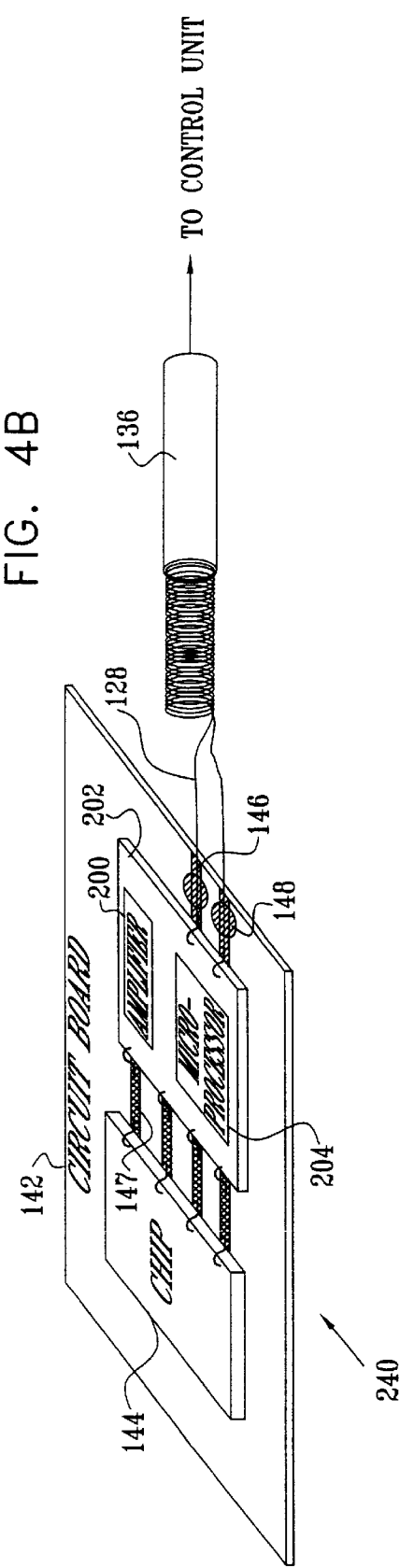

FIG. 4B is a schematic drawing of a connection system 240, in accordance with a preferred embodiment of the present invention. System 240 is generally similar to system 140, described hereinabove with reference to FIG. 4A, except for differences as noted. Circuit board 142 comprises a signal processor 202, which, in turn, comprises a microprocessor 204 and an amplifier 200. Amplifier 200 preferably amplifies a voltage drop v(t) generated during operation of chip 144 (e.g., responsive to pressure changes applied to a piezoresistive element), and microprocessor 204 digitizes the amplified signal. Advantageously, the number of wires 128 coupling control unit 102 to circuit board 142 can by these means be reduced, with no loss in functionality. In a preferred embodiment, only two wires 128 couple control unit 102 to microprocessor 204, and these wires carry power to the microprocessor, in order to facilitate the microprocessor's operations. For example, the microprocessor may be coupled to the control unit by the two wires 128, and to a pressure sensor 114 in chip 144 by four conductors 147. Results of the pressure sensing are then preferably conveyed by microprocessor 204 to the control unit by applying a modulation signal onto the two wires 128 that carry power to the microprocessor. Further advantageously, when circuit board 142 includes a microprocessor, especially in combination with an amplifier, the noise which might otherwise corrupt a low-amplitude analog signal to some extent during its propagation to control unit 102 is substantially reduced.

It is noted in this respect that these aspects of connection system 240 may be incorporated into catheter apparatus (not shown), or other non-implanted sensing or active devices, so as to benefit from the reduced signal noise and wire-count which are attainable by performing processing at the actual sensed or treated site. By contrast, standard techniques perform substantially all of their processing remote from the sensed or treated site. In a preferred embodiment, a catheter has a pressure sensor, microprocessor, and amplifier, at the distal end thereof, constructed using techniques described herein, and conveys digitized pressure readings to a control unit external to the patient's body, preferably via only two leads coupling the microprocessor and the control unit.

FIG. 5 is a sectional schematic drawing of an implantable device 160, in accordance with a preferred embodiment of the present invention. Device 160 includes chip 124, which preferably contains a pressure-sensing element, and connection system 120 to transmit pressure data to a control unit (not shown), as described hereinabove with reference to FIGS. 3A and 3B. Applications other than pressure sensing, such as those described with reference to FIGS. 3A and 3B, may be alternatively or additionally incorporated into device 160. Thus, for example, device 160 may include an implantable temperature or chemical sensor, or an implantable electrode.

A stainless steel cylinder 166 is used to protect the chip and the connection system during implantation in the body, and, subsequently, from the physiological environment inside the patient's body. Cylinder 166 provides a rigid surface to which to fasten circuit board 122, thus providing a stable base for chip 124, which includes pressure-sensing apparatus. Preferably, a UV-hardened glue 172 is used to increase the mechanical strength of connections in the device. A pressure-sensing hole 168 is present in cylinder 166, typically adjacent to the pressure-sensing apparatus of chip 124, so that the pressure of the surrounding tissue can be sensed. Hole 168 may be, for example, 1.8 mm in diameter.

Two fill holes 170 in cylinder 166 are used to fill cylinder 166 with a pressure transducing substance, preferably a silicon gel 174. A plurality of holes are used so that as gel 174 is fed in one hole 170, any trapped air or excess gel can exit the other hole 170 or hole 168. It is preferred to remove all air bubbles from cylinder 166 in order to obtain a uniform medium in the cylinder and thereby facilitate the accurate measurement of the pressure external to cylinder 166. Electrical components inside cylinder 166 are protected from moisture by a thin coating such as parylene, typically several microns deep. To maintain the integrity of gel 174 and prevent contaminants from the body from entering cylinder 166 through hole 168 or holes 170, cylinder 166 is preferably encased in a flexible covering such as a flexible tube 162, capable of conveying body pressures to the pressure sensing apparatus inside cylinder 166. In a preferred embodiment, tube 162 includes silicon, and a silicon glue cap 164 is placed at one end of tube 166 following the placement of the gel in cylinder 166. Moreover, the flexible covering is preferably largely non-metallic.

It is noted that the method described in this preferred embodiment of the present invention for filling gel 174 in one hole while allowing it to escape through another hole, followed by placing a flexible tube around the pressure chamber (cylinder 166) stands in contrast to many techniques known in the art for building implantable pressure sensors. In accordance with these prior art techniques, a pressure chamber is filled with a gel, after which a thin, fragile, metal plate is placed over the chamber. Disadvantages associated with these prior art techniques include difficulties in removing air bubbles from the gel, as well as the need to take extra measures to avoid damaging the thin metal plate.

In a preferred embodiment, the apparatus or methods described herein for measuring physiological pressures, for other sensing tasks, or for applying currents or for other active tasks, are used to facilitate corresponding operations, such as those described in the above-cited U.S. patent application, entitled, "Pelvic disorder treatment device," filed Nov. 29, 2001, which shares common inventorship with the inventorship of the present patent application, is assigned to the assignee of the present patent application, and is incorporated herein by reference.

It is noted that whereas some preferred embodiments of the present invention are described with respect to implantable apparatus by way of illustration and not limitation, the scope of the present invention includes non-implantable apparatus as well. For example, pressure transducers described herein as implantable may also be incorporated into catheters.

It is also noted that whereas some techniques of the present invention are described hereinabove with respect to a pressure transducer, this is by way of illustration and not limitation. The scope of the present invention includes using the techniques described herein with other medical apparatus, such as medical sensors or medical active devices.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. Pressure-measuring apparatus, comprising:
   a battery;
   a pressure transducer, which is adapted to be placed in a patient, the pressure transducer having a characteristic mechanical response bandwidth f, and a corresponding mechanical response period p equal to 1/f; and
   a control unit, which is adapted to actuate the battery to drive current through the pressure transducer for a current-driving time period less than 0.5 p, and to sense an electrical characteristic of the pressure transducer during the current-driving time period.

2. Apparatus according to claim 1, wherein the pressure transducer is adapted to be implanted in the patient.

3. Apparatus according to claim 1, wherein the pressure transducer is adapted to be incorporated in a catheter.

4. Apparatus according to claim 1, wherein the pressure transducer is adapted to measure an abdominal pressure of the patient.

5. Apparatus according to claim 1, wherein the pressure transducer is adapted to measure a pressure of a urinary bladder of the patient.

6. Apparatus according to claim 1, wherein the pressure transducer is adapted to measure a cardiac pressure of the patient.

7. Apparatus according to claim 1, where in the pressure transducer is adapted to measure a blood pressure of the patient.

8. Apparatus according to claim 1, wherein the pressure transducer comprises a piezoresistive pressure transducer.

9. Apparatus according to claim 1, wherein the pressure transducer comprises a Wheatstone bridge circuit.

10. Apparatus according to claim 1, wherein the control unit is adapted to set the current-driving time period to be less than 1000 microseconds.

11. Apparatus according to claim 1, wherein the control unit is adapted to designate an initial portion of the current-driving time period as a pressure-transducer stabilization period, during which the control unit withholds from sensing the characteristic.

12. Apparatus according to claim 1, wherein the control unit is adapted to include, in sensing the electrical characteristic, sensing a current passing through the pressure transducer.

13. Apparatus according to claim 1, wherein the control unit is adapted to include, in sensing the electrical characteristic, sensing a voltage drop across two points of the pressure transducer.

14. Apparatus according to claim 1, wherein the control unit is adapted to sense the electrical characteristic substantially only during the current-driving time period.

15. Apparatus according to claim 1, wherein the control unit is adapted to actuate the battery to expend less than 5 microjoules in driving the current through the pressure transducer.

16. Apparatus according to claim 1, wherein the control unit is adapted to actuate the battery to drive the current directly into the pressure transducer, substantially without charging a capacitor located at a placement site of the pressure transducer.

17. Apparatus according to claim 1, wherein the control unit is adapted to actuate the battery to drive the current directly into the pressure transducer, substantially without charging a capacitor located at a placement site of the pressure transducer having capacitance greater than 0.1 nF.

18. Apparatus according to claim 1,
wherein the control unit is adapted to actuate the battery to drive current into the pressure transducer during a plurality of current-driving time periods, each less than 0.5 p, and to sense respective electrical characteristics of the pressure transducer during each of the current-driving time periods, and
wherein the battery is adapted to drive the current directly into the pressure transducer, substantially without charging a capacitor located at a placement site of the pressure transducer during each of the current-driving time periods.

19. Apparatus according to claim 1,
wherein the control unit is adapted to actuate the battery to drive current through the pressure transducer during a plurality of current-driving time periods, each less than 0.5 p, and
wherein a duty cycle of the control unit defined by a length of one of the current-driving time periods divided by a time between the initiation of two successive current-driving time periods is less than 0.3%.

20. Apparatus according to claim 19, wherein the duty cycle of the control unit is less than 0.03%.

21. Apparatus according to claim 1, wherein the control unit is adapted to designate an initial portion of the current-driving time period as a pressure-transducer stabilization period, and to sense the electrical characteristic of the pressure transducer at least in part during the stabilization period.

22. Apparatus according to claim 21, wherein the control unit is adapted to designate the stabilization period to be less than 1 microsecond.

23. Apparatus according to claim 21, wherein the control unit is adapted to sense the electrical characteristic of the pressure transducer exclusively during the stabilization period.

24. Apparatus according to claim 21, wherein the control unit is adapted to process the sensed electrical characteristic responsive to a portion of the stabilization period in which it was sensed.

25. Apparatus according to claim 24, wherein the control unit is adapted to apply a correcting factor to the sensed electrical characteristic responsive to the portion of the stabilization period in which it was sensed.

26. Apparatus according to claim 1, and comprising a signal processor, adapted to be placed in the patient at a common placement site with the pressure transducer and to process the sensed electrical characteristic.

27. Apparatus according to claim 26, wherein the signal processor comprises an amplifier, adapted to amplify the sensed electrical characteristic.

28. Apparatus according to claim 26, wherein the signal processor comprises a microprocessor.

29. Apparatus according to claim 28, and comprising:
a first set of wires, adapted to couple the control unit to the microprocessor; and
a second set of wires, adapted to couple the microprocessor to the pressure transducer,
wherein the number of wires in the second set of wires is greater than the number of wires in the first set of wires.

30. Apparatus according to claim 1, wherein the control unit is adapted to set the current-driving time period to be less than 0.1 p.

31. Apparatus according to claim 30, wherein the control unit is adapted to set the current-driving time period to be less than 0.02 p.

32. Apparatus according to claim 31, wherein the control unit is adapted to set the current-driving time period to be less than 0.004 p.

33. Apparatus according to claim 1, wherein the control unit is adapted to: (a) actuate the battery to drive current through the pressure transducer during a plurality of current-driving time periods, each less than 0.5 p, (b) sense respective electrical characteristics of the pressure transducer during each of the current-driving time periods, and (c) space the current-driving time periods by at least ten milliseconds.

34. Apparatus according to claim 33, wherein the control unit is adapted to space the current-driving time periods by at least one second.

35. Apparatus according to claim 34, wherein the control unit is adapted to space the current-driving time periods by at least one minute.

36. Apparatus according to claim 35, wherein the control unit is adapted to space the current-driving time periods by at least one hour.

37. Pressure-measuring apparatus, comprising:
a pressure transducer, which is adapted to be placed at a pressure-sensing site in a patient, the pressure transducer having a characteristic mechanical response bandwidth f, and a corresponding mechanical response period p equal to 1/f; and
a control unit, adapted to be placed at a control-unit site at least 3 cm from the pressure-sensing site, to drive current through the pressure transducer for a current-driving time period less than 0.5 p, and to sense an electrical characteristic of the pressure transducer during the current-driving time period.

38. Apparatus according to claim 37, wherein the control unit is adapted to be placed at a control-unit site which is at least 5 cm from the pressure-sensing site.

39. Apparatus according to claim 37, wherein the pressure transducer is adapted to be implanted in the patient.

40. Apparatus according to claim 37, wherein the pressure transducer is adapted to be incorporated in a catheter.

41. Apparatus according to claim 37, wherein the pressure transducer is adapted to measure an abdominal pressure of the patient.

42. Apparatus according to claim 37, wherein the pressure transducer is adapted to measure a pressure of a urinary bladder of the patient.

43. Apparatus according to claim 37, wherein the pressure transducer is adapted to measure a cardiac pressure of the patient.

44. Apparatus according to claim 37, wherein the pressure transducer is adapted to measure a blood pressure of the patient.

45. Apparatus according to claim 37, wherein the pressure transducer comprises a piezoresistive pressure transducer.

46. Apparatus according to claim 37, wherein the pressure transducer comprises a Wheatstone bridge circuit.

47. Apparatus according to claim 37, wherein the control unit is adapted to set the current-driving time period to be less than 1000 microseconds.

48. Apparatus according to claim 37, wherein the control unit is adapted to designate an initial portion of the current-driving time period as a pressure-transducer stabilization period, during which the control unit withholds from sensing the characteristic.

49. Apparatus according to claim 37, wherein the control unit is adapted to include, in sensing the electrical characteristic, sensing a current passing through the pressure transducer.

50. Apparatus according to claim 37, wherein the control unit is adapted to include, in sensing the electrical characteristic, sensing a voltage drop across two points of the pressure transducer.

51. Apparatus according to claim 37, wherein the control unit is adapted to sense the electrical characteristic substantially only during the current-driving time period.

52. Apparatus according to claim 37, wherein the control unit is adapted to expend less than 5 microjoules in driving the current through the pressure transducer.

53. Apparatus according to claim 37, wherein the control unit is adapted to drive the current directly into the pressure transducer, substantially without charging a capacitor located at a placement site of the pressure transducer.

54. Apparatus according to claim 37, wherein the control unit is adapted to drive the current directly into the pressure transducer, substantially without charging a capacitor located with the pressure transducer at the pressure-sensing site having capacitance greater than 0.1 nF.

55. Apparatus according to claim 37,
wherein the control unit is adapted to drive current into the pressure transducer during a plurality of current-driving time periods, each less than 0.5 p, and to sense respective electrical characteristics of the pressure transducer during each of the current-driving time periods, and
wherein the control unit is adapted to drive the current directly into the pressure transducer, substantially without charging a capacitor located with the pressure transducer at the pressure-sensing site during each of the current-driving time periods.

56. Apparatus according to claim 37,
wherein the control unit is adapted to drive current through the pressure transducer during a plurality of current-driving time periods, each less than 0.5 p, and
wherein a duty cycle of the control unit defined by a length of one of the current-driving time periods divided by a time between the initiation of two successive current-driving time periods is less than 0.3%.

57. Apparatus according to claim 56, wherein the duty cycle of the control unit is less than 0.03%.

58. Apparatus according to claim 37, wherein the control unit is adapted to designate an initial portion of the current-driving time period as a pressure-transducer stabilization period, and to sense the electrical characteristic of the pressure transducer at least in part during the stabilization period.

59. Apparatus according to claim 58, wherein the control unit is adapted to designate the stabilization period to be less than 1 microsecond.

60. Apparatus according to claim 58, wherein the control unit is adapted to sense the electrical characteristic of the pressure transducer exclusively during the stabilization period.

61. Apparatus according to claim 58, wherein the control unit is adapted to process the sensed electrical characteristic responsive to a portion of the stabilization period in which it was sensed.

62. Apparatus according to claim 61, wherein the control unit is adapted to apply a correcting factor to the sensed electrical characteristic responsive to the portion of the stabilization period in which it was sensed.

63. Apparatus according to claim 37, and comprising a signal processor, adapted to be placed in the patient at the pressure-sensing site and to process the sensed electrical characteristic.

64. Apparatus according to claim 63, wherein the signal processor comprises an amplifier, adapted to amplify the sensed electrical characteristic.

65. Apparatus according to claim 63, wherein the signal processor comprises a microprocessor.

66. Apparatus according to claim 65, and comprising:
a first set of wires, adapted to couple the control unit to the microprocessor; and
a second set of wires, adapted to couple the microprocessor to the pressure transducer,
wherein the number of wires in the second set of wires is greater than the number of wires in the first set of wires.

67. Apparatus according to claim 37, wherein the control unit is adapted to set the current-driving time period to be less than 0.1 p.

68. Apparatus according to claim 67, wherein the control unit is adapted to set the current-driving time period to be less than 0.02 p.

69. Apparatus according to claim 68, wherein the control unit is adapted to set the current-driving time period to be less than 0.004 p.

70. Apparatus according to claim 37, wherein the control unit is adapted to: (a) drive current through the pressure transducer during a plurality of current-driving time periods, each less than 0.5 p, (b) sense respective electrical characteristics of the pressure transducer during each of the current-driving time periods, and (c) space the current-driving time periods by at least ten milliseconds.

71. Apparatus according to claim 70, wherein the control unit is adapted to space the current-driving time periods by at least one second.

72. Apparatus according to claim 71, wherein the control unit is adapted to space the current-driving time periods by at least one minute.

73. Apparatus according to claim 72, wherein the control unit is adapted to space the current-driving time periods by at least one hour.

74. Pressure-measuring apparatus, comprising:
a battery;
a pressure transducer, which is adapted to be placed in a patient; and
a control unit, which is adapted to actuate the battery to drive current through the pressure transducer for a current-driving time period less than 1000 microseconds, and to sense an electrical characteristic of the pressure transducer during the current-driving time period.

75. Apparatus according to claim 74, wherein the pressure transducer is adapted to be implanted in the patient.

76. Apparatus according to claim 74, wherein the pressure transducer is adapted to be incorporated in a catheter.

77. Apparatus according to claim 74, wherein the pressure transducer is adapted to measure an abdominal pressure of the patient.

78. Apparatus according to claim 74, wherein the pressure transducer is adapted to measure a pressure of a urinary bladder of the patient.

79. Apparatus according to claim 74, wherein the pressure transducer is adapted to measure a cardiac pressure of the patient.

80. Apparatus according to claim 74, wherein the pressure transducer is adapted to measure a blood pressure of the patient.

81. Apparatus according to claim 74, wherein the pressure transducer comprises a piezoresistive pressure transducer.

82. Apparatus according to claim 74, wherein the control unit is adapted to designate an initial portion of the current-driving time period as a pressure-transducer stabilization period, during which the control unit withholds from sensing the characteristic.

83. Apparatus according to claim 74, wherein the control unit is adapted to include, in sensing the electrical characteristic, sensing a current passing through the pressure transducer.

84. Apparatus according to claim 74, wherein the control unit is adapted to include, in sensing the electrical characteristic, sensing a voltage drop across two points of the pressure transducer.

85. Apparatus according to claim 74, wherein the control unit is adapted to sense the electrical characteristic substantially only during the current-driving time period.

86. Apparatus according to claim 74, wherein the control unit is adapted to actuate the battery to expend less than 5 microjoules in driving the current through the pressure transducer.

87. Apparatus according to claim 74, wherein the control unit is adapted to actuate the battery to drive the current directly into the pressure transducer, substantially without charging a capacitor located at a placement site of the pressure transducer.

88. Apparatus according to claim 74, wherein the control unit is adapted to actuate the battery to drive the current directly into the pressure transducer, substantially without charging a capacitor located at a placement site of the pressure transducer having capacitance greater than 0.1 nF.

89. Apparatus according to claim 74,
wherein the control unit is adapted to actuate the battery to drive current into the pressure transducer during a plurality of current-driving time periods, each less than 1000 microseconds, and to sense respective electrical characteristics of the pressure transducer during each of the current-driving time periods, and
wherein the battery is adapted to drive the current directly into the pressure transducer, substantially without charging a capacitor located at a placement site of the pressure transducer during each of the current-driving time periods.

90. Apparatus according to claim 74,
wherein the control unit is adapted to actuate the battery to drive current through the pressure transducer during a plurality of current-driving time periods, each less than 1000 microseconds, and
wherein a duty cycle of the control unit defined by a length of one of the current-driving time periods divided by a time between the initiation of two successive current-driving time periods is less than 0.3%.

91. Apparatus according to claim 90, wherein the duty cycle of the control unit is less than 0.03%.

92. Apparatus according to claim 74, wherein the control unit is adapted to designate an initial portion of the current-driving time period as a pressure-transducer stabilization period, and to sense the electrical characteristic of the pressure transducer at least in part during the stabilization period.

93. Apparatus according to claim 92, wherein the control unit is adapted to designate the stabilization period to be less than 1 microsecond.

94. Apparatus according to claim 92, wherein the control unit is adapted to sense the electrical characteristic of the pressure transducer exclusively during the stabilization period.

95. Apparatus according to claim 92, wherein the control unit is adapted to process the sensed electrical characteristic responsive to a portion of the stabilization period in which it was sensed.

96. Apparatus according to claim 95, wherein the control unit is adapted to apply a correcting factor to the sensed electrical characteristic responsive to the portion of the stabilization period in which it was sensed.

97. Apparatus according to claim 74, and comprising a signal processor, adapted to be placed in the patient at a common placement site with the pressure transducer and to process the sensed electrical characteristic.

98. Apparatus according to claim 97, wherein the signal processor comprises an amplifier, adapted to amplify the sensed electrical characteristic.

99. Apparatus according to claim 97, wherein the signal processor comprises a microprocessor.

100. Apparatus according to claim 99, and comprising:
a first set of wires, adapted to couple the control unit to the microprocessor; and
a second set of wires, adapted to couple the microprocessor to the pressure transducer,
wherein the number of wires in the second set of wires is greater than the number of wires in the first set of wires.

101. Apparatus according to claim 74, wherein the control unit is adapted to: (a) actuate the battery to drive current through the pressure transducer during a plurality of current-driving time periods, each less than 1000 microseconds, (b) sense respective electrical characteristics of the pressure transducer during each of the current-driving time periods, and (c) space the current-driving time periods by at least ten milliseconds.

102. Apparatus according to claim 101, wherein the control unit is adapted to space the current-driving time periods by at least one second.

103. Apparatus according to claim 102, wherein the control unit is adapted to space the current-driving time periods by at least one minute.

104. Apparatus according to claim 103, wherein the control unit is adapted to space the current-driving time periods by at least one hour.

105. Apparatus according to claim 74, wherein the control unit is adapted to set the current-driving time period to be less than 250 microseconds.

106. Apparatus according to claim 105, wherein the control unit is adapted to set the current-driving time period to be less than 50 microseconds.

107. Apparatus according to claim 106, wherein the control unit is adapted to set the current-driving time period to be less than 10 microseconds.

108. Apparatus according to claim 107, wherein the control unit is adapted to set the current-driving time period to be less than 2 microseconds.

109. Pressure-measuring apparatus, comprising:
a pressure transducer, which is adapted to be placed at a pressure-sensing site in a patient; and
a control unit, adapted to be placed at a control-unit site at least 3 cm from the pressure-sensing site, to drive current through the pressure transducer for a current-driving time period less than 1000 microseconds, and to sense an electrical characteristic of the pressure transducer during the current-driving time period.

110. Apparatus according to claim 109, wherein the control unit is adapted to be placed at a control-unit site which is at least 5 cm from the pressure-sensing site.

111. Apparatus according to claim 109, wherein the pressure transducer is adapted to be implanted in the patient.

112. Apparatus according to claim 109, wherein the pressure transducer is adapted to be incorporated in a catheter.

113. Apparatus according to claim 109, wherein the pressure transducer is adapted to measure an abdominal pressure of the patient.

114. Apparatus according to claim 109, wherein the pressure transducer is adapted to measure a pressure of a urinary bladder of the patient.

115. Apparatus according to claim 109, wherein the pressure transducer is adapted to measure a cardiac pressure of the patient.

116. Apparatus according to claim 109, wherein the pressure transducer is adapted to measure a blood pressure of the patient.

117. Apparatus according to claim 109, wherein the pressure transducer comprises a piezoresistive pressure transducer.

118. Apparatus according to claim 109, wherein the control unit is adapted to designate an initial portion of the current-driving time period as a pressure-transducer stabilization period, during which the control unit withholds from sensing the characteristic.

119. Apparatus according to claim 109, wherein the control unit is adapted to include, in sensing the electrical characteristic, sensing a current passing through the pressure transducer.

120. Apparatus according to claim 109, wherein the control unit is adapted to include, in sensing the electrical characteristic, sensing a voltage drop across two points of the pressure transducer.

121. Apparatus according to claim 109, wherein the control unit is adapted to sense the electrical characteristic substantially only during the current-driving time period.

122. Apparatus according to claim 109, wherein the control unit is adapted to expend less than 5 microjoules in driving the current through the pressure transducer.

123. Apparatus according to claim 109, wherein the control unit is adapted to drive the current directly into the pressure transducer, substantially without charging a capacitor located at a placement site of the pressure transducer.

124. Apparatus according to claim 109, wherein the control unit is adapted to drive the current directly into the pressure transducer, substantially without charging a capacitor located with the pressure transducer at the pressure-sensing site having capacitance greater than 0.1 nF.

125. Apparatus according to claim 109,
wherein the control unit is adapted to drive current into the pressure transducer during a plurality of current-driving time periods, each less than 1000 microseconds, and to sense respective electrical characteristics of the pressure transducer during each of the current-driving time periods, and
wherein the control unit is adapted to drive the current directly into the pressure transducer, substantially without charging a capacitor located with the pressure transducer at the pressure-sensing site during each of the current-driving time periods.

126. Apparatus according to claim 109,
wherein the control unit is adapted to drive current through the pressure transducer during a plurality of current-driving time periods, each less than 1000 microseconds, and
wherein a duty cycle of the control unit defined by a length of one of the current-driving time periods divided by a time between the initiation of two successive current-driving time periods is less than 0.3%.

127. Apparatus according to claim 126, wherein the duty cycle of the control unit is less than 0.03%.

128. Apparatus according to claim 109, wherein the control unit is adapted to designate an initial portion of the current-driving time period as a pressure-transducer stabilization period, and to sense the electrical characteristic of the pressure transducer at least in part during the stabilization period.

129. Apparatus according to claim 128, wherein the control unit is adapted to designate the stabilization period to be less than 1 microsecond.

130. Apparatus according to claim 128, wherein the control unit is adapted to sense the electrical characteristic of the pressure transducer exclusively during the stabilization period.

131. Apparatus according to claim 128, wherein the control unit is adapted to process the sensed electrical characteristic responsive to a portion of the stabilization period in which it was sensed.

132. Apparatus according to claim 131, wherein the control unit is adapted to apply a correcting factor to the sensed electrical characteristic responsive to the portion of the stabilization period in which it was sensed.

133. Apparatus according to claim 109, and comprising a signal processor, adapted to be placed in the patient at the pressure-sensing site and to process the sensed electrical characteristic.

134. Apparatus according to claim 133, wherein the signal processor comprises an amplifier, adapted to amplify the sensed electrical characteristic.

135. Apparatus according to claim 133, wherein the signal processor comprises a microprocessor.

136. Apparatus according to claim 135, and comprising:
a first set of wires, adapted to couple the control unit to the microprocessor; and
a second set of wires, adapted to couple the microprocessor to the pressure transducer,
wherein the number of wires in the second set of wires is greater than the number of wires in the first set of wires.

137. Apparatus according to claim 109, wherein the control unit is adapted to: (a) drive current through the pressure transducer during a plurality of current-driving time periods, each less than 1000 microseconds, (b) sense respective electrical characteristics of the pressure transducer during each of the current-driving time periods, and (c) space the current-driving time periods by at least ten milliseconds.

138. Apparatus according to claim 137, wherein the control unit is adapted to space the current-driving time periods by at least one second.

139. Apparatus according to claim 138, wherein the control unit is adapted to space the current-driving time periods by at least one minute.

140. Apparatus according to claim 139, wherein the control unit is adapted to space the current-driving time periods by at least one hour.

141. Apparatus according to claim 109, wherein the control unit is adapted to set the current-driving time period to be less than 250 microseconds.

142. Apparatus according to claim 141, wherein the control unit is adapted to set the current-driving time period to be less than 50 microseconds.

143. Apparatus according to claim 142, wherein the control unit is adapted to set the current-driving time period to be less than 10 microseconds.

144. A method for measuring pressure via a pressure transducer, placed in a patient, the pressure transducer having a characteristic mechanical response bandwidth f, and a corresponding mechanical response period p equal to 1/f, the pressure transducer being coupled to a battery, the method comprising:
actuating the battery to drive current through the pressure transducer for a current-driving time period less than 0.5 p; and
sensing an electrical characteristic of the pressure transducer during the current-driving time period.

145. A method according to claim 144, wherein the method is practiced via a pressure transducer implanted in the patient.

146. A method according to claim 144, wherein the method is practiced via a pressure transducer incorporated in a catheter.

147. A method according to claim 144, wherein the method comprises measuring an abdominal pressure of the patient.

148. A method according to claim 144, wherein the method comprises measuring a pressure of a urinary bladder of the patient.

149. A method according to claim 144, wherein the method comprises measuring a cardiac pressure of the patient.

150. A method according to claim 144, wherein the method comprises measuring a blood pressure of the patient.

151. A method according to claim 144, wherein the method comprises measuring pressure via a piezoresistive pressure transducer.

152. A method according to claim 144, wherein actuating the battery comprises setting the current-driving time period to be less than 1000 microseconds.

153. A method according to claim 144, wherein actuating the battery comprises:
designating an initial portion of the current-driving time period as a pressure-transducer stabilization period; and
withholding from sensing the characteristic during the stabilization period.

154. A method according to claim 144, wherein sensing the electrical characteristic comprises sensing a current passing through the pressure transducer.

155. A method according to claim 144, wherein sensing the electrical characteristic comprises sensing a voltage drop across two points of the pressure transducer.

156. A method according to claim 144, wherein sensing the electrical characteristic comprises sensing the electrical characteristic substantially only during the current-driving time period.

157. A method according to claim 144, wherein actuating the battery comprises actuating the battery to expend less than 5 microjoules in driving the current through the pressure transducer.

158. A method according to claim 144, wherein actuating the battery comprises actuating the battery to drive the current directly into the pressure transducer, substantially without charging a capacitor located at a placement site of the pressure transducer.

159. A method according to claim 144, wherein actuating the battery comprises actuating the battery to drive the current directly into the pressure transducer, substantially without charging a capacitor located at a placement site of the pressure transducer having capacitance greater than 0.1 nF.

160. A method according to claim 144,
wherein actuating the battery comprises actuating the battery to drive current into the pressure transducer during a plurality of current-driving time periods, each less than 0.5 p,
wherein actuating the battery comprises actuating the battery to drive the current directly into the pressure transducer, substantially without charging a capacitor located at a placement site of the pressure transducer during each of the current-driving time periods, and
wherein sensing the electrical characteristic comprises sensing respective electrical characteristics of the pressure transducer during each of the current-driving time periods.

161. A method according to claim 144, wherein actuating the battery comprises:
actuating the battery to drive current through the pressure transducer during a plurality of current-driving time periods, each less than 0.5 p; and
setting a duty cycle, defined by a length of one of the current-driving time periods divided by a time between the initiation of two successive current-driving time periods, to be less than 0.3%.

162. A method according to claim 161, wherein setting the duty cycle comprises setting the duty cycle to be less than 0.03%.

163. A method according to claim 144, wherein an initial portion of the current-driving time period is designated as a pressure-transducer stabilization period, and wherein sensing the electrical characteristic of the pressure transducer comprises sensing the electrical characteristic at least in part during the stabilization period.

164. A method according to claim 163, wherein the stabilization period is designated to be less than 1 microsecond.

165. A method according to claim 163, wherein sensing the electrical characteristic of the pressure transducer occurs exclusively during the stabilization period.

166. A method according to claim 163, and comprising processing the sensed electrical characteristic responsive to a portion of the stabilization period in which it was sensed.

167. A method according to claim 166, wherein processing comprises applying a correcting factor to the sensed electrical characteristic responsive to the portion of the stabilization period in which it was sensed.

168. A method according to claim 144, and comprising processing the sensed electrical characteristic at a placement site of the pressure transducer.

169. A method according to claim 168, wherein processing the sensed electrical characteristic comprises amplifying the sensed electrical characteristic.

170. A method according to claim 144, wherein actuating the battery comprises setting the current-driving time period to be less than 0.1 p.

171. A method according to claim 170, wherein actuating the battery comprises setting the current-driving time period to be less than 0.02 p.

172. A method according to claim 171, wherein actuating the battery comprises setting the current-driving time period to be less than 0.004 p.

173. A method according to claim 144,
wherein actuating the battery comprises actuating the battery to drive current through the pressure transducer during a plurality of current-driving time periods, each less than 0.5 p, and spacing the current-driving time periods by at least ten milliseconds, and
wherein sensing the electrical characteristic comprises sensing respective electrical characteristics of the pressure transducer during each of the current-driving time periods.

174. A method according to claim 173, wherein spacing the current-driving time periods comprises spacing the current-driving time periods by at least one second.

175. A method according to claim 174, wherein spacing the current-driving time periods comprises spacing the current-driving time periods by at least one minute.

176. A method according to claim 175, wherein spacing the current-driving time periods comprises spacing the current-driving time periods by at least one hour.

177. A method for measuring pressure via a pressure transducer, placed in a patient at a pressure-sensing site, the pressure transducer having a characteristic mechanical response bandwidth f, and a corresponding mechanical response period p equal to 1/f, the method comprising:
from a control-unit site at least 3 cm from the pressure-sensing site, driving current through the pressure transducer for a current-driving time period less than 0.5 p; and
sensing an electrical characteristic of the pressure transducer during the current-driving time period.

178. A method according to claim 177, wherein driving the current comprises driving the current from a control-unit site which is at least 5 cm from the pressure-sensing site.

179. A method according to claim 177, wherein the method is practiced via a pressure transducer implanted in the patient.

180. A method according to claim 177, wherein the method is practiced via a pressure transducer incorporated in a catheter.

181. A method according to claim 177, wherein the method comprises measuring an abdominal pressure of the patient.

182. A method according to claim 177, wherein the method comprises measuring a pressure of a urinary bladder of the patient.

183. A method according to claim 177, wherein the method comprises measuring a cardiac pressure of the patient.

184. A method according to claim 177, wherein the method comprises measuring a blood pressure of the patient.

185. A method according to claim 177, wherein the method comprises measuring pressure via a piezoresistive pressure transducer.

186. A method according to claim 177, wherein driving the current comprises setting the current-driving time period to be less than 1000 microseconds.

187. A method according to claim 177, wherein driving the current comprises:
designating an initial portion of the current-driving time period as a pressure-transducer stabilization period; and
withholding from sensing the characteristic during the stabilization period.

188. A method according to claim 177, wherein sensing the electrical characteristic comprises sensing a current passing through the pressure transducer.

189. A method according to claim 177, wherein sensing the electrical characteristic comprises sensing a voltage drop across two points of the pressure transducer.

190. A method according to claim 177, wherein sensing the electrical characteristic comprises sensing the electrical characteristic substantially only during the current-driving time period.

191. A method according to claim 177, wherein driving the current comprises expending less than 5 microjoules in driving the current through the pressure transducer.

192. A method according to claim 177, wherein driving the current comprises driving the current directly into the pressure transducer, substantially without charging a capacitor located at a placement site of the pressure transducer.

193. A method according to claim 177, wherein driving the current comprises driving the current directly into the pressure transducer, substantially without charging a capacitor located with the pressure transducer at the pressure-sensing site having capacitance greater than 0.1 nF.

194. A method according to claim 177,
wherein driving the current comprises driving the current into the pressure transducer during a plurality of current-driving time periods, each less than 0.5 p,
wherein driving the current comprises driving the current directly into the pressure transducer, substantially without charging a capacitor located at a placement site of the pressure transducer during each of the current-driving time periods, and
wherein sensing the electrical characteristic comprises sensing respective electrical characteristics of the pressure transducer during each of the current-driving time periods.

195. A method according to claim 177, wherein driving the current comprises:
driving the current through the pressure transducer during a plurality of current-driving time periods, each less than 0.5 p; and
setting a duty cycle, defined by a length of one of the current-driving time periods divided by a time between the initiation of two successive current-driving time periods, to be less than 0.3%.

196. A method according to claim 195, wherein setting the duty cycle comprises setting the duty cycle to be less than 0.03%.

197. A method according to claim 177, wherein an initial portion of the current-driving time period is designated as a pressure-transducer stabilization period, and wherein sensing the electrical characteristic of the pressure transducer comprises sensing the electrical characteristic at least in part during the stabilization period.

198. A method according to claim 197, wherein the stabilization period is designated to be less than 1 microsecond.

199. A method according to claim 197, wherein sensing the electrical characteristic of the pressure transducer occurs exclusively during the stabilization period.

200. A method according to claim 197, and comprising processing the sensed electrical characteristic responsive to a portion of the stabilization period in which it was sensed.

201. A method according to claim 200, wherein processing comprises applying a correcting factor to the sensed electrical characteristic responsive to the portion of the stabilization period in which it was sensed.

202. A method according to claim 177, and comprising processing the sensed electrical characteristic at the pressure-sensing site.

203. A method according to claim 202, wherein processing the sensed electrical characteristic comprises amplifying the sensed electrical characteristic.

204. A method according to claim 177, wherein driving the current comprises setting the current-driving time period to be less than 0.1 p.

205. A method according to claim 204, wherein driving the current comprises setting the current-driving time period to be less than 0.02 p.

206. A method according to claim 205, wherein driving the current comprises setting the current-driving time period to be less than 0.004 p.

207. A method according to claim 177,
wherein driving the current comprises driving the current through the pressure transducer during a plurality of current-driving time periods, each less than 0.5 p, and spacing the current-driving time periods by at least ten milliseconds, and
wherein sensing the electrical characteristic comprises sensing respective electrical characteristics of the pressure transducer during each of the current-driving time periods.

208. A method according to claim 207, wherein spacing the current-driving time periods comprises spacing the current-driving time periods by at least one second.

209. A method according to claim 208, wherein spacing the current-driving time periods comprises spacing the current-driving time periods by at least one minute.

210. A method according to claim 209, wherein spacing the current-driving time periods comprises spacing the current-driving time periods by at least one hour.

211. A method for measuring pressure via a pressure transducer, placed in a patient, the pressure transducer being coupled to a battery, the method comprising:
actuating the battery to drive current through the pressure transducer for a current-driving time period less than 1000 microseconds; and
sensing an electrical characteristic of the pressure transducer during the current-driving time period.

212. A method according to claim 211, wherein the method is practiced via a pressure transducer implanted in the patient.

213. A method according to claim 211, wherein the method is practiced via a pressure transducer incorporated in a catheter.

214. A method according to claim 211, wherein the method comprises measuring an abdominal pressure of the patient.

215. A method according to claim 211, wherein the method comprises measuring a pressure of a urinary bladder of the patient.

216. A method according to claim 211, wherein the method comprises measuring a cardiac pressure of the patient.

217. A method according to claim 211, wherein the method comprises measuring a blood pressure of the patient.

218. A method according to claim 211, wherein the method comprises measuring pressure via a piezoresistive pressure transducer.

219. A method according to claim 211, wherein actuating the battery comprises:
designating an initial portion of the current-driving time period as a pressure-transducer stabilization period; and
withholding from sensing the characteristic during the stabilization period.

220. A method according to claim 211, wherein sensing the electrical characteristic comprises sensing a current passing through the pressure transducer.

221. A method according to claim 211, wherein sensing the electrical characteristic comprises sensing a voltage drop across two points of the pressure transducer.

222. A method according to claim 211, wherein sensing the electrical characteristic comprises sensing the electrical characteristic substantially only during the current-driving time period.

223. A method according to claim 211, wherein actuating the battery comprises actuating the battery to expend less than 5 microjoules in driving the current through the pressure transducer.

224. A method according to claim 211, wherein actuating the battery comprises actuating the battery to drive the current directly into the pressure transducer, substantially without charging a capacitor located at a placement site of the pressure transducer.

225. A method according to claim 211, wherein actuating the battery comprises actuating the battery to drive the current directly into the pressure transducer, substantially without charging a capacitor located at a placement site of the pressure transducer having capacitance greater than 0.1 nF.

226. A method according to claim 211,
wherein actuating the battery comprises actuating the battery to drive current into the pressure transducer during a plurality of current-driving time periods, each less than 1000 microseconds,
wherein actuating the battery comprises actuating the battery to drive the current directly into the pressure transducer, substantially without charging a capacitor located at a placement site of the pressure transducer during each of the current-driving time periods, and
wherein sensing the electrical characteristic comprises sensing respective electrical characteristics of the pressure transducer during each of the current-driving time periods.

227. A method according to claim 211, wherein actuating the battery comprises:
actuating the battery to drive current through the pressure transducer during a plurality of current-driving time periods, each less than 1000 microseconds; and
setting a duty cycle, defined by a length of one of the current-driving time periods divided by a time between the initiation of two successive current-driving time periods, to be less than 0.3%.

228. A method according to claim 227, wherein setting the duty cycle comprises setting the duty cycle to be less than 0.03%.

229. A method according to claim 211, wherein an initial portion of the current-driving time period is designated as a pressure-transducer stabilization period, and wherein sensing the electrical characteristic of the pressure transducer comprises sensing the electrical characteristic at least in part during the stabilization period.

230. A method according to claim 229, wherein the stabilization period is designated to be less than 1 microsecond.

231. A method according to claim 229, wherein sensing the electrical characteristic of the pressure transducer occurs exclusively during the stabilization period.

232. A method according to claim 229, and comprising processing the sensed electrical characteristic responsive to a portion of the stabilization period in which it was sensed.

233. A method according to claim 232, wherein processing comprises applying a correcting factor to the sensed electrical characteristic responsive to the portion of the stabilization period in which it was sensed.

234. A method according to claim 211, and comprising processing the sensed electrical characteristic at a placement site of the pressure transducer.

235. A method according to claim 234, wherein processing the sensed electrical characteristic comprises amplifying the sensed electrical characteristic.

236. A method according to claim 211,
wherein actuating the battery comprises actuating the battery to drive current through the pressure transducer during a plurality of current-driving time periods, each less than 1000 microseconds, and spacing the current-driving time periods by at least ten milliseconds, and
wherein sensing the electrical characteristic comprises sensing respective electrical characteristics of the pressure transducer during each of the current-driving time periods.

237. A method according to claim 236, wherein spacing the current-driving time periods comprises spacing the current-driving time periods by at least one second.

238. A method according to claim 237, wherein spacing the current-driving time periods comprises spacing the current-driving time periods by at least one minute.

239. A method according to claim 238, wherein spacing the current-driving time periods comprises spacing the current-driving time periods by at least one hour.

240. A method according to claim 211, wherein actuating the battery comprises setting the current-driving time period to be less than 250 microseconds.

241. A method according to claim 240, wherein actuating the battery comprises setting the current-driving time period to be less than 50 microseconds.

242. A method according to claim 241, wherein actuating the battery comprises setting the current-driving time period to be less than 10 microseconds.

243. A method according to claim 242, wherein actuating the battery comprises setting the current-driving time period to be less than 2 microseconds.

244. A method for measuring pressure via a pressure transducer, placed in a patient at a pressure-sensing site, the method comprising:
from a control-unit site at least 3 cm from the pressure-sensing site, driving current through the pressure transducer for a current-driving time period less than 1000 microseconds; and
sensing an electrical characteristic of the pressure transducer during the current-driving time period.

245. A method according to claim 244, wherein driving the current comprises driving the current from a control-unit site which is at least 5 cm from the pressure-sensing site.

246. A method according to claim 244, wherein the method is practiced via a pressure transducer implanted in the patient.

247. A method according to claim 244, wherein the method is practiced via a pressure transducer incorporated in a catheter.

248. A method according to claim 244, wherein the method comprises measuring an abdominal pressure of the patient.

249. A method according to claim 244, wherein the method comprises measuring a pressure of a urinary bladder of the patient.

250. A method according to claim 244, wherein the method comprises measuring a cardiac pressure of the patient.

251. A method according to claim 244, wherein the method comprises measuring a blood pressure of the patient.

252. A method according to claim 244, wherein the method comprises measuring pressure via a piezoresistive pressure transducer.

253. A method according to claim 244, wherein driving the current comprises:
designating an initial portion of the current-driving time period as a pressure-transducer stabilization period; and
withholding from sensing the characteristic during the stabilization period.

254. A method according to claim 244, wherein sensing the electrical characteristic comprises sensing a current passing through the pressure transducer.

255. A method according to claim 244, wherein sensing the electrical characteristic comprises sensing a voltage drop across two points of the pressure transducer.

256. A method according to claim 244, wherein sensing the electrical characteristic comprises sensing the electrical characteristic substantially only during the current-driving time period.

257. A method according to claim 244, wherein driving the current comprises expending less than 5 microjoules in driving the current through the pressure transducer.

258. A method according to claim 244, wherein driving the current comprises driving the current directly into the pressure transducer, substantially without charging a capacitor located at a placement site of the pressure transducer.

259. A method according to claim 244, wherein driving the current comprises driving the current directly into the pressure transducer, substantially without charging a capacitor located with the pressure transducer at the pressure-sensing site having capacitance greater than 0.1 nF.

260. A method according to claim 244,
wherein driving the current comprises driving the current into the pressure transducer during a plurality of current-driving time periods, each less than 1000 microseconds,
wherein driving the current comprises driving the current directly into the pressure transducer, substantially without charging a capacitor located at a placement site of the pressure transducer during each of the current-driving time periods, and
wherein sensing the electrical characteristic comprises sensing respective electrical characteristics of the pressure transducer during each of the current-driving time periods.

261. A method according to claim 244, wherein driving the current comprises:
driving the current through the pressure transducer during a plurality of current-driving time periods, each less than 1000 microseconds; and
setting a duty cycle, defined by a length of one of the current-driving time periods divided by a time between the initiation of two successive current-driving time periods, to be less than 0.3%.

262. A method according to claim 261, wherein setting the duty cycle comprises setting the duty cycle to be less than 0.03%.

263. A method according to claim 244, wherein an initial portion of the current-driving time period is designated as a pressure-transducer stabilization period, and wherein sensing the electrical characteristic of the pressure transducer comprises sensing the electrical characteristic at least in part during the stabilization period.

264. A method according to claim 263, wherein the stabilization period is designated to be less than 1 microsecond.

265. A method according to claim 263, wherein sensing the electrical characteristic of the pressure transducer occurs exclusively during the stabilization period.

266. A method according to claim 263, and comprising processing the sensed electrical characteristic responsive to a portion of the stabilization period in which it was sensed.

267. A method according to claim 266, wherein processing comprises applying a correcting factor to the sensed electrical characteristic responsive to the portion of the stabilization period in which it was sensed.

268. A method according to claim 244, and comprising processing the sensed electrical characteristic at the pressure-sensing site.

269. A method according to claim 268, wherein processing the sensed electrical characteristic comprises amplifying the sensed electrical characteristic.

270. A method according to claim 244,
wherein driving the current comprises driving the current through the pressure transducer during a plurality of current-driving time periods, each less than 1000 microseconds, and spacing the current-driving time periods by at least ten milliseconds, and
wherein sensing the electrical characteristic comprises sensing respective electrical characteristics of the pressure transducer during each of the current-driving time periods.

271. A method according to claim 270, wherein spacing the current-driving time periods comprises spacing the current-driving time periods by at least one second.

272. A method according to claim 271, wherein spacing the current-driving time periods comprises spacing the current-driving time periods by at least one minute.

273. A method according to claim 272, wherein spacing the current-driving time periods comprises spacing the current-driving time periods by at least one hour.

274. A method according to claim 244, wherein driving the current comprises setting the current-driving time period to be less than 250 microseconds.

275. A method according to claim 274, wherein driving the current comprises setting the current-driving time period to be less than 50 microseconds.

276. A method according to claim 275, wherein driving the current comprises setting the current-driving time period to be less than 10 microseconds.

* * * * *